United States Patent
Tono et al.

(10) Patent No.: US 12,318,571 B2
(45) Date of Patent: Jun. 3, 2025

(54) MEDICAL DEVICE PACKAGING CONTAINER AND PACKAGED MEDICAL DEVICE

(71) Applicant: TERUMO KABUSHIKI KAISHA, Tokyo (JP)

(72) Inventors: Yohei Tono, Chuo (JP); Satoru Matsunaga, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 157 days.

(21) Appl. No.: 18/206,370

(22) Filed: Jun. 6, 2023

(65) Prior Publication Data
US 2023/0310734 A1 Oct. 5, 2023

Related U.S. Application Data

(63) Continuation of application No. PCT/JP2021/043657, filed on Nov. 29, 2021.

(30) Foreign Application Priority Data

Dec. 9, 2020 (JP) ................. 2020-203901

(51) Int. Cl.
*A61M 5/00* (2006.01)
*B65D 1/36* (2006.01)
(Continued)

(52) U.S. Cl.
CPC .............. *A61M 5/002* (2013.01); *B65D 1/36* (2013.01); *B65D 75/366* (2013.01); *B65D 75/5855* (2013.01)

(58) Field of Classification Search
CPC ............... A61M 5/002; A61M 25/002; A61M 2209/06; A61M 5/001; A61M 5/3202;
(Continued)

(56) References Cited

U.S. PATENT DOCUMENTS 2,786,882 A * 3/1957 Krefft ................. H01J 5/32
313/332
3,255,880 A * 6/1966 Grossman .......... A61M 25/002
D9/415
(Continued)

FOREIGN PATENT DOCUMENTS

EP 0 398 316 A1 11/1990
JP S38-12598 B1 7/1963
(Continued)

OTHER PUBLICATIONS

Extended European Search Report issued in connection with European Appl. No. 21903218.2 dated Sep. 6, 2023.
(Continued)

*Primary Examiner* — Steven A. Reynolds
*Assistant Examiner* — Prince Pal
(74) *Attorney, Agent, or Firm* — Foley & Lardner LLP

(57) ABSTRACT

A medical device packaging container includes a tray, a sheet-like lid portion having an annular flange portion, and an annular heat seal portion. The annular heat seal portion includes a first-side seal portion, a second-side seal portion, a third-side seal portion, and a fourth-side seal portion. The first-side seal portion includes a central seal portion, a first side-part seal portion, and a second side-part seal portion. The central seal portion includes central seal extension portions, the first side-part seal portion includes a first side-part seal extension portion, and the second side-part seal portion includes a second side-part seal extension portion.

20 Claims, 8 Drawing Sheets

(51) Int. Cl.
  *B65D 75/36* (2006.01)
  *B65D 75/58* (2006.01)

(58) Field of Classification Search
  CPC . A61B 50/30; A61B 50/33; A61B 2050/3006; A61B 2050/3008; A61B 50/34; B65D 75/326; B65D 77/2032; B65D 77/2024; B65D 25/04; B65D 2575/3245; B65D 75/5855; B65D 75/30
  USPC ....... 206/438, 571, 570, 569, 364, 363, 210, 206/365; 604/187
  See application file for complete search history.

(56) References Cited

U.S. PATENT DOCUMENTS

| | | | | |
|---|---|---|---|---|
| 3,419,137 | A * | 12/1968 | Walck, III | B65D 75/5855 426/123 |
| 3,460,742 | A * | 8/1969 | Langdon | A61M 5/002 206/439 |
| 3,927,762 | A * | 12/1975 | Zdarsky | B65D 75/28 206/229 |
| RE29,678 | E * | 6/1978 | Antonini | A61B 18/1402 206/363 |
| 4,106,621 | A * | 8/1978 | Sorenson | B65D 75/328 229/125.35 |
| 4,184,593 | A * | 1/1980 | Dorr | A61M 5/002 604/227 |
| 4,226,328 | A * | 10/1980 | Beddow | A61F 17/00 D24/114 |
| 4,355,755 | A * | 10/1982 | Faller | B65D 1/40 229/406 |
| 4,730,726 | A * | 3/1988 | Holzwarth | B65D 81/268 206/230 |
| 4,736,850 | A * | 4/1988 | Bowman | A61F 2/0095 206/370 |
| 4,811,847 | A * | 3/1989 | Reif | A61B 42/40 206/278 |
| 4,946,038 | A * | 8/1990 | Eaton | B65D 77/206 229/123.1 |
| 5,082,112 | A * | 1/1992 | Dunklee | A61B 50/30 206/363 |
| 5,111,932 | A * | 5/1992 | Campbell | B65D 75/48 206/229 |
| 5,133,454 | A * | 7/1992 | Hammer | A61M 5/3205 206/364 |
| 5,156,267 | A * | 10/1992 | Yates, Jr. | A61M 5/3205 220/4.23 |
| 5,300,038 | A * | 4/1994 | Haber | A61M 5/322 604/272 |
| 5,379,895 | A * | 1/1995 | Foslien | A61B 50/30 206/363 |
| 5,386,908 | A * | 2/1995 | Sinn | A61B 17/06133 206/363 |
| 5,392,909 | A * | 2/1995 | Hackett | A61B 50/3001 206/451 |
| 5,392,918 | A * | 2/1995 | Harrison | A61B 50/30 206/370 |
| 5,407,070 | A * | 4/1995 | Bascos | A61M 5/002 206/467 |
| 5,485,917 | A * | 1/1996 | Early | A61B 50/30 206/363 |
| 5,566,828 | A * | 10/1996 | Claes | A61M 5/003 206/570 |
| 5,688,544 | A * | 11/1997 | Bolton | B65D 77/225 426/123 |
| 5,690,222 | A * | 11/1997 | Peters | B65D 77/26 206/592 |
| 5,772,031 | A * | 6/1998 | Landis | A61B 50/30 206/363 |
| 5,842,567 | A * | 12/1998 | Rowe | A61B 50/3001 206/464 |
| 5,947,284 | A * | 9/1999 | Foster | A61B 50/30 206/364 |
| 6,010,462 | A * | 1/2000 | Stoermer, III | B65D 77/245 600/572 |
| D430,015 | S * | 8/2000 | Himbert | D24/227 |
| 6,228,324 | B1 * | 5/2001 | Hasegawa | A61L 2/208 604/199 |
| 6,499,595 | B1 * | 12/2002 | Petricca | B65D 1/40 53/412 |
| 6,793,078 | B2 * | 9/2004 | Roshdy | A61B 50/33 206/459.5 |
| 6,814,236 | B2 * | 11/2004 | Roshdy | A61B 50/33 206/363 |
| 6,866,151 | B2 * | 3/2005 | Mousset | A61B 50/31 206/570 |
| 6,915,901 | B2 * | 7/2005 | Feinberg | A61B 17/00491 206/363 |
| 6,920,978 | B2 * | 7/2005 | Fischer | B65D 1/36 206/499 |
| 6,994,213 | B2 * | 2/2006 | Giard, Jr. | A61B 5/150503 206/363 |
| 7,597,196 | B2 * | 10/2009 | Langone | A61M 5/002 206/364 |
| 7,815,123 | B2 * | 10/2010 | Conner | A61L 2/28 235/487 |
| 7,901,383 | B2 * | 3/2011 | Follman | A61B 5/150358 604/189 |
| 7,954,636 | B2 * | 6/2011 | Vincent-Aubry | A61F 2/1678 623/6.12 |
| 8,113,348 | B2 * | 2/2012 | Foster | A61B 50/20 206/478 |
| 8,308,363 | B2 * | 11/2012 | Vogt | B65D 50/00 383/203 |
| 8,584,849 | B2 * | 11/2013 | McCaffrey | A61M 25/002 206/364 |
| 8,727,117 | B2 * | 5/2014 | Maasarani | A61M 5/002 206/364 |
| D709,767 | S * | 7/2014 | Morrison | D9/456 |
| 8,770,409 | B2 * | 7/2014 | Cude | B65D 21/0204 206/557 |
| 9,150,342 | B2 * | 10/2015 | Sierra-Gomez | B65D 77/206 |
| 9,926,116 | B2 * | 3/2018 | Kinyon | B65D 51/00 |
| 10,172,682 | B2 * | 1/2019 | Van Der Raad-Meijer | B65D 75/366 |
| D906,102 | S * | 12/2020 | Cook | D9/737 |
| 11,160,918 | B2 * | 11/2021 | Cook | B65B 69/005 |
| 11,432,817 | B2 * | 9/2022 | Barton | A61B 50/30 |
| 11,542,136 | B1 * | 1/2023 | May | A61J 1/16 |
| 11,660,385 | B1 * | 5/2023 | Thakore | B65D 65/22 206/364 |
| 11,738,171 | B2 * | 8/2023 | Glithero | A61M 25/0017 206/571 |
| 11,820,565 | B2 * | 11/2023 | McDonald | G06K 7/1413 |
| D1,037,850 | S * | 8/2024 | Kelley | D9/732 |
| 12,133,963 | B2 * | 11/2024 | Dumont | A61M 5/002 |
| 12,151,035 | B2 * | 11/2024 | Ryan | B65D 25/04 |
| 2001/0007926 | A1 * | 7/2001 | Trudil | A61B 10/0096 206/569 |
| 2002/0108875 | A1 * | 8/2002 | Feinberg | A61B 17/00491 206/364 |
| 2003/0034264 | A1 * | 2/2003 | Hamai | A61M 5/002 422/26 |
| 2003/0159968 | A1 * | 8/2003 | McMichael | A61B 50/30 206/570 |
| 2004/0238391 | A1 * | 12/2004 | Pond | A61C 19/02 206/369 |
| 2005/0211595 | A1 * | 9/2005 | Hull | A61B 50/30 206/363 |
| 2006/0058599 | A1 * | 3/2006 | Cummings | A61B 5/257 600/391 |
| 2006/0275336 | A1 * | 12/2006 | Du Plessis | A61L 2/0011 604/82 |
| 2007/0074990 | A1 * | 4/2007 | Merboth | A61B 90/94 206/438 |
| 2008/0097306 | A1 * | 4/2008 | Smith | A61M 5/1782 604/110 |

(56) References Cited

U.S. PATENT DOCUMENTS

| | | | | | |
|---|---|---|---|---|---|
| 2008/0108936 | A1* | 5/2008 | Timm | | A61P 27/16 604/21 |
| 2008/0125721 | A1* | 5/2008 | Timm | | A61P 27/06 220/500 |
| 2008/0135443 | A1* | 6/2008 | Frojd | | A61M 25/0606 206/571 |
| 2008/0240627 | A1* | 10/2008 | Cole | | B65D 77/2096 383/204 |
| 2008/0302697 | A1* | 12/2008 | Cude | | A61M 5/002 220/4.27 |
| 2009/0149527 | A1* | 6/2009 | Timm | | A61K 31/407 206/572 |
| 2009/0194446 | A1* | 8/2009 | Miller | | A61B 50/33 606/86 R |
| 2010/0018974 | A1* | 1/2010 | Lyzenga | | B65D 43/0235 220/214 |
| 2010/0181218 | A1* | 7/2010 | Beccaro | | A61F 9/0017 604/218 |
| 2010/0219092 | A1* | 9/2010 | Salahieh | | B65D 81/22 206/438 |
| 2012/0118777 | A1* | 5/2012 | Kakiuchi | | A61M 5/002 29/428 |
| 2012/0125932 | A1* | 5/2012 | Sierra-Gomez | | B65D 75/5838 220/255 |
| 2012/0145589 | A1* | 6/2012 | Macinnes | | A61B 50/30 53/411 |
| 2012/0197218 | A1* | 8/2012 | Timm | | A61B 50/33 604/294 |
| 2012/0227358 | A1* | 9/2012 | Larson | | B65B 7/2842 53/111 R |
| 2013/0284629 | A1* | 10/2013 | Kinyon | | A61F 2/0095 206/438 |
| 2014/0013718 | A1* | 1/2014 | Maasarani | | B65D 77/2032 206/364 |
| 2014/0224688 | A1* | 8/2014 | Slemmen | | A61M 5/3204 206/365 |
| 2014/0262880 | A1* | 9/2014 | Yoon | | A61B 50/30 53/469 |
| 2015/0021221 | A1* | 1/2015 | Hendrickson | | A61B 50/20 206/438 |
| 2015/0076023 | A1* | 3/2015 | Kinyon | | B65D 51/00 206/438 |
| 2015/0224247 | A1* | 8/2015 | McDorman | | A61B 50/20 206/569 |
| 2015/0335855 | A1* | 11/2015 | Tomes | | A61B 50/30 206/571 |
| 2016/0016714 | A1* | 1/2016 | Fenech, III | | B65D 65/40 428/494 |
| 2016/0122109 | A1* | 5/2016 | Clark | | B65D 75/5888 220/23.4 |
| 2016/0135895 | A1* | 5/2016 | Faasse | | B65B 55/02 53/425 |
| 2016/0375199 | A1* | 12/2016 | Ward | | A61M 5/3202 604/506 |
| 2017/0008686 | A1* | 1/2017 | Tanoguchi | | B65D 75/326 |
| 2017/0143893 | A1* | 5/2017 | Hasumi | | A61M 5/3202 |
| 2018/0085515 | A1* | 3/2018 | Mide | | A61M 5/002 |
| 2019/0001049 | A1* | 1/2019 | Bianco | | A61M 5/002 |
| 2019/0307911 | A1* | 10/2019 | Bala | | A61L 2/208 |
| 2020/0047963 | A1* | 2/2020 | Caleman | | B32B 29/02 |
| 2020/0289742 | A1* | 9/2020 | Pfrang | | A61J 7/0053 |
| 2020/0338259 | A1* | 10/2020 | Mainz | | A61B 50/30 |
| 2021/0030945 | A1* | 2/2021 | Cook | | A61M 5/002 |
| 2021/0077645 | A1* | 3/2021 | Mismar | | A61L 2/26 |
| 2022/0033160 | A1* | 2/2022 | Hasumi | | B65D 77/2064 |
| 2022/0081179 | A1* | 3/2022 | Rey | | B65B 5/068 |
| 2022/0097914 | A1* | 3/2022 | Küçük | | B65D 77/2024 |
| 2022/0133426 | A1* | 5/2022 | O'Flynn | | B65D 81/22 206/210 |
| 2022/0133981 | A1* | 5/2022 | Dumont | | B65B 5/04 206/364 |
| 2022/0161983 | A1* | 5/2022 | Cardin | | B65D 75/5855 |
| 2022/0175979 | A1* | 6/2022 | Ryan | | B65D 25/04 |
| 2023/0105267 | A1* | 4/2023 | Sutto | | B65D 77/204 220/270 |
| 2023/0248898 | A1* | 8/2023 | Cook | | A61L 2/206 604/500 |
| 2023/0310734 | A1* | 10/2023 | Tono | | B65D 1/36 206/438 |
| 2023/0329821 | A1* | 10/2023 | McClure | | A61B 10/02 |
| 2023/0413975 | A1* | 12/2023 | Holley | | B65D 25/108 |
| 2025/0032699 | A1* | 1/2025 | Duff | | A61K 31/7036 |
| 2025/0058001 | A1* | 2/2025 | Ryan | | A61L 2/0005 |

FOREIGN PATENT DOCUMENTS

| | | |
|---|---|---|
| JP | S59-199463 A | 11/1984 |
| JP | 2786882 B2 | 8/1998 |
| JP | 2000-335641 A | 12/2000 |
| JP | 2001-104475 A | 4/2001 |
| JP | 2006-168769 A | 6/2006 |
| JP | 2007-297080 A | 11/2007 |
| JP | 2008-150112 A | 7/2008 |
| JP | 2008-179411 A | 8/2008 |
| JP | 2017-013805 A | 1/2017 |
| WO | WO-96/19383 A1 | 6/1996 |

OTHER PUBLICATIONS

International Searching Authority, "International Search Report," issued in connection with International Patent Application No. PCT/JP2021/043657, dated Jan. 25, 2022.

International Searching Authority, "Written Opinion," issued in connection with International Patent Application No. PCT/JP2021/043657, dated Jan. 25, 2022.

International Searching Authority, "Written Opinion," issued in connection with International Patent Application No. PCT/JP2021/043657, dated Jan. 25, 2022 (with English translation).

* cited by examiner

MEDICAL DEVICE PACKAGING CONTAINER AND PACKAGED MEDICAL DEVICE

CROSS-REFERENCE TO RELATED APPLICATIONS

The is a bypass continuation of PCT Application No. PCT/JP2021/043657, filed on Nov. 29, 2021, which claims priority to Japanese Application No. 2020-203901, filed on Dec. 9, 2020. The contents of these applications are incorporated herein by reference in their entireties.

BACKGROUND

The present disclosure relates to a medical device packaging container and a packaged medical device packaged by the medical device packaging container. Specifically, the present disclosure relates to a blister-type medical device packaging container and a packaged medical device that are easy to open.

In the related art, packaging containers for storing many medical devices have been used, and many medical devices have been provided in a packaged state. As the packaging container, there is a bag-like packaging container, a so-called blister-type packaging container.

In blister packaging, a tray (container main body) and a sheet-like lid portion (sealing film) peelably adhered to a top surface opening portion of the tray are provided. The tray includes an annular flange formed on a peripheral edge of the opening portion, and the sheet-like lid portion is peelably fixed to the annular flange by an annular heat seal portion.

In such a blister packaging container, the tray is often formed in a long rectangular shape in terms of the shape of the medical device as a storage object. For this reason, the outer edge of the flange of the tray is also formed in a rectangular annular shape in many cases.

The rectangular annular flange generally has four corners, and the corners are curved. In a case where the flange of the tray has a rectangular annular shape, the heat seal portion formed on the flange also has a rectangular annular shape.

As a shape of a heat seal portion in such blister packaging, the applicant of the present application proposes Japanese Patent No. 2786882 (EP 0398316 A1) ("Patent Literature 1"), JP 2001-104475 A ("Patent Literature 2"), and JP S59-199463 A ("Patent Literature 3"). Furthermore, J P 2007-297080 ("Patent Literature 4") also discloses a shape of a heat seal portion.

SUMMARY

In the packaging container of Patent Literature 1 (Japanese Patent No. 2786882), a packaging container 11 includes a tray portion 15 and a synthetic resin sheet-like lid 16. The tray portion 15 is formed by a sheet made of a synthetic resin and in a tray-like rectangle 12 having curved portions at four containers, and includes a flange portion 14 having an outer edge 13 parallel to the rectangular tray-like shape in a peripheral edge of the opening portion.

The tray portion 15 and the lid 16 are thermally fused and sealed in a belt-like shape 17 with a predetermined width via an adhesive layer formed on the inner surface of the lid. The lid 16 is formed so as to protrude outward with respect to the outer edge 13 of the flange portion 14 of the tray portion 15 at all four corners thereof.

In FIG. 3 of Patent Literature 1, four corner portions of the rectangular lid 16 are curved at a curvature radius smaller than a curvature radius of an outer edge virtual line 13 of the flange portion 14 parallel to the peripheral edge of the opening portion of the tray portion 15 corresponding to the four corner portions, and preferably curved at about half the curvature radius of the outer edge virtual line 13, and thus protruding portions are formed. Furthermore, it is also disclosed that taking into consideration that a person easily peels off the heat seal portion in a state in which the seal strength and seal width between a tray inner layer and a lid material are constant, as a shape of the protruding portion at the time of starting of peeling off, it is advantageous that the distal end of the protruding portion is sharpened.

In Patent Literature 2 (JP 2001-104475), a packaged prefilled syringe 1 is illustrated in FIG. 12. In the packaged prefilled syringe 1, a non-seal portion 51 for gripping when peeling off a sealing film 22 at the time of use is provided on the rear end side of a plunger 14 of a syringe 5. A seal portion includes a first seal portion 52, a second seal portion 53, and a third seal portion 54 from the non-seal portion 51 side. Although the width of the first seal portion 52 is narrower than those of the other seal portions, the first seal portion 52 has sufficient seal strength because the first seal portion 52 is fully sealed, and resistance at the time of peeling off is not so large. Moreover, the corner portion of the first seal portion 52 is recessed inward such that the first seal portion 52 is less likely to be partially peeled off even when an external force is applied from the corner of the non-seal portion 51 before use.

Patent Literature 3 (JP S59-199463 A) discloses the following.

As illustrated in FIGS. 5 to 6 of Patent Literature 3, at least one corner portion is defined as a peeling start portion 14, and an adhesive portion 11 is formed so as to protrude outward with respect to a peeling force action line X-X" of the lid 15 at the corner portion. In the case of FIG. 6, because a plurality of (for example, three) protruding distal end portions 18 are formed, the protruding distal end portions have a waveform, and it is desirable that each protruding distal end portion 18 (protrusion) is located at substantially the same distance (radius R3) from a center point Y, and an outer protrusion position R2 and an inner protrusion position R1 satisfy R1≤R2. FIG. 7 of Patent Literature 3 illustrates another embodiment of the packaging container, and similarly, in the adhesive portion 11 formed so as to protrude outward with respect to the peeling force action line of the lid 15, a protruding distal end portion 18 of the central portion protrudes most outward at a position of a line a, the protruding distal end portions 18 of the both end portions protrude outward at a position of a line b, an inner recess of the central portion is formed at a portion of a line c, inner recesses of the both end portions are formed at a position of a line d, and inner protrusions are formed at a position of a line e, and the peeling off is extremely easy due to such arrangement.

Patent Literature 4 (JP 2007-297080 A) discloses the following.

(Object) To provide a packaging container that is easy to open and capable of ensuring sufficient adhesive strength.

(Solution) In a packaging container 100 in which a rectangular opening portion 4 of a base material 1, in which a recess 3 for storing an article is formed downward, is covered by a sheet-like member 2, a flange portion 10 extending outward in a horizontal direction from a peripheral edge of the opening portion 4 is provided, the sheet-like member 2 is adhered to an adhesive region 111 on an upper surface of the flange portion 10 to seal an inside of the base material 1, at least one of four corners of the opening portion 4 is set as an opening corner portion C, and a non-adhesive region 112c, which is not adhered to the sheet-like member 2, is provided outside an adhesive region 111c of the opening corner portion C to form a knob portion 5 at the time of opening, the adhesive region 111c of the opening corner portion C is formed so as to be raised upward.

The peeling off of the sheet-like lid portion in the blister packaging is performed by gripping a part of the sheet-like lid portion and pulling the part of the sheet-like lid portion in a predetermined direction. The direction of pulling the sheet-like lid portion for peeling off the sheet-like lid portion is different depending on an operator, and is not uniform. For example, in a case where the peeling off is started by gripping the peeling start portion of the sheet-like lid portion and pulling the peeling start portion substantially in a direction parallel to a longitudinal direction of the tray, or in a case where the peeling off is performed by gripping the peeling start portion of the sheet-like lid portion and pulling the peeling start portion obliquely in the longitudinal direction of the tray from a first corner portion of the tray close to the peeling start portion, it is assumed that the peeling start portion of the sheet-like lid portion is griped, and then the peeling off is performed by pulling the peeling start portion obliquely in the longitudinal direction of the tray from a second corner portion opposite to the first corner portion of the tray and close to the peeling start portion.

However, in Patent Literatures 1 to 4, which are described above, the sheet-like lid portion is peeled off from the corner portion in the blister packaging, and there is no description that the peeling start portion of the sheet-like lid portion is gripped and the peeling start portion is pulled substantially in a direction parallel to the longitudinal direction of the tray.

Furthermore, there is a case where a protrusion of a heat seal portion is provided in order to facilitate the peeling-off. However, a so-called protrusion facilitates the peeling-off, but may cause unintended peeling-off.

An object of certain embodiments of the present disclosure is to provide a medical device packaging container in which the sheet-like lid portion can be satisfactorily peeled off from the tray even when the peeling-off of the sheet-like lid portion is started from any of the above-described directions, and that does not have a seal fragility portion caused due to a shape of the heat seal portion, and a medical device packaged by the packaging container.

The object described above is achieved by the following.
A medical device packaging container including:
a tray having an upper end opening portion and a medical device storage portion; and
a sheet-like lid portion that closes the upper end opening portion of the tray,
in which the tray includes an annular flange portion provided on an entire periphery of the upper end opening portion,
the packaging container includes an annular heat seal portion that peelably fixes the sheet-like lid portion on the annular flange portion and has a rectangular outer edge,
the annular heat seal portion includes a first-side seal portion and a second-side seal portion, which are opposite to each other, and a third-side seal portion and a fourth-side seal portion, which are positioned between the first-side seal portion and the second-side seal portion and opposite to each other,
the sheet-like lid portion includes a flap portion protruding from the first-side seal portion of the annular heat seal portion,
one end of the third-side seal portion and one end of the fourth-side seal portion are positioned on the second-side seal portion side by a predetermined length with respect to the first-side seal portion,
the first-side seal portion includes a central seal portion, a first side-part seal portion extending obliquely and connecting one end of the central seal portion with the one end of the third-side seal portion, and a second side-part seal portion extending obliquely and connecting the other end of the central seal portion and the one end of the fourth-side seal portion,
the first-side seal portion includes a plurality of central seal extension portions extending from an outer edge of the central seal portion and separated from each other by a predetermined length, a first side-part seal extension portion extending from an outer edge of the first side-part seal portion, and a second side-part seal extension portion extending from an outer edge of the second side-part seal portion,
an outer edge of a distal end portion of the central seal extension portion, an outer edge of a distal end portion of the first side-part seal extension portion, and an outer edge of a distal end portion of the second side-part seal extension portion have a rounded shape without corners, and
a distance between the one end and the other end of the central seal portion is 45/100 to 55/100 of a distance between an outer edge of the one end of the third-side seal portion and an outer edge of the one end of the fourth-side seal portion.

Furthermore, the object described above is achieved by the following.

A packaged medical device including: the medical device packaging container described above; and a medical device stored in the medical device storage portion of the tray, in which the upper end opening portion of the tray is peelably sealed by the sheet-like lid portion in a state in which the medical device is stored.

DETAILED DESCRIPTION

An embodiment of a medical device packaging container and a packaged medical device according to the present disclosure will be described with reference to drawings.

Figure 1:
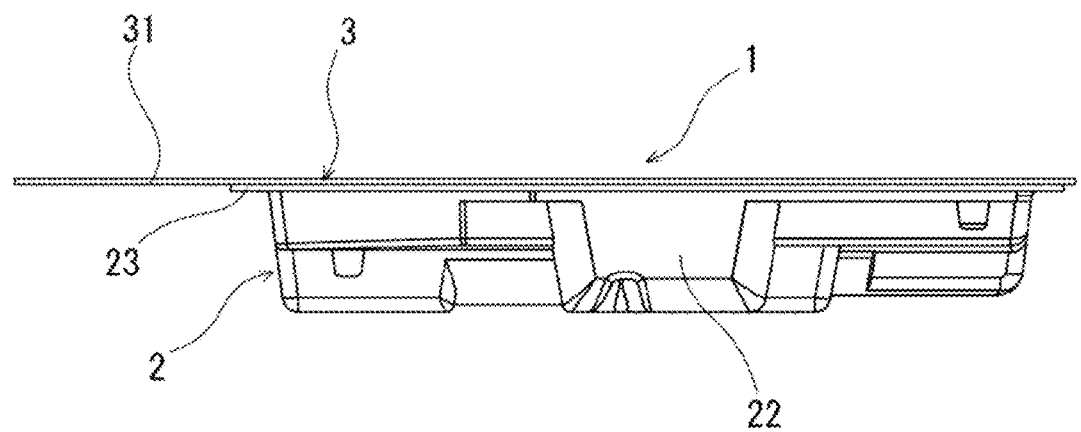
FIG. 1 is a front view of a medical device packaging container and a packaged medical device according to an embodiment of the present disclosure.
Figure 2:
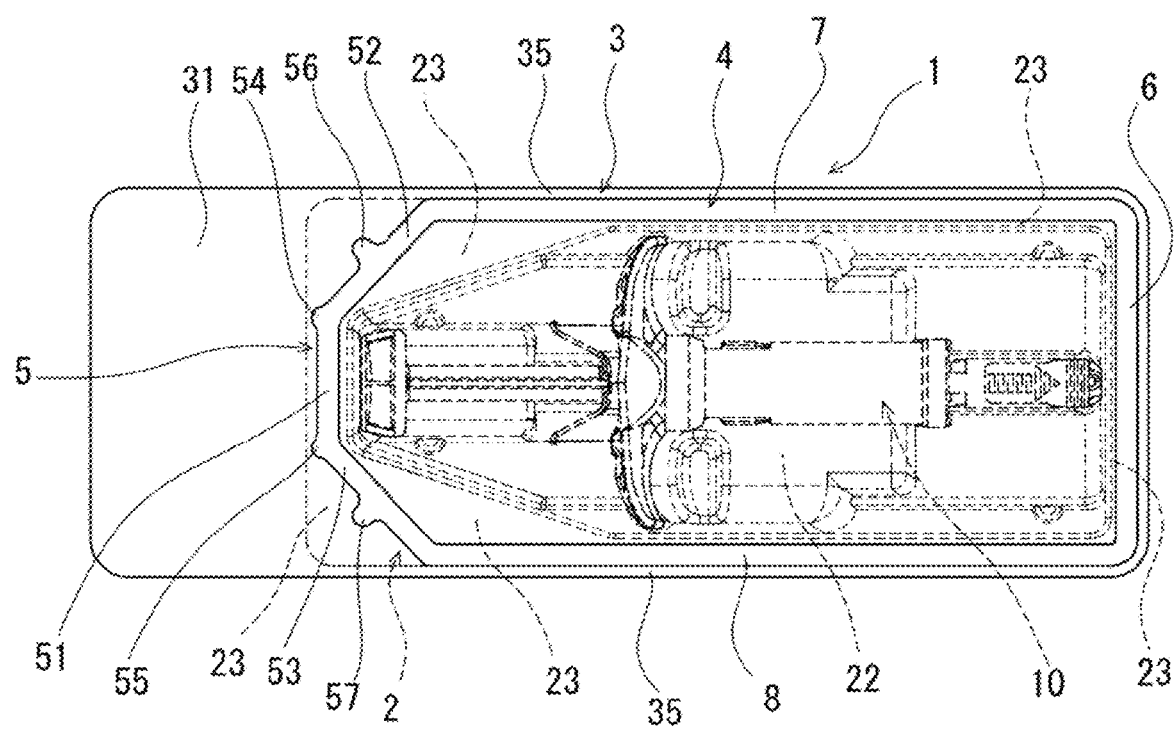
FIG. 2 is a plan view illustrating the medical device packaging container and the packaged medical device according to an embodiment of the present disclosure, which are illustrated in FIG. 1.
Figure 3:
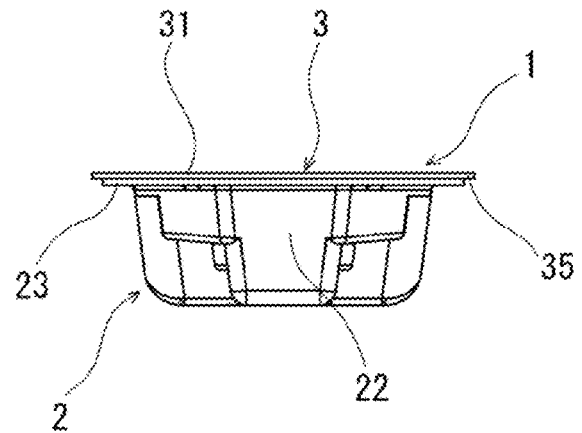
FIG. 3 is a left side view illustrating the medical device packaging container and the packaged medical device according to an embodiment of the present disclosure, which are illustrated in FIG. 1.

As illustrated in FIGS. 1 to 3, a medical device packaging container 1 according to an embodiment of the present disclosure includes: a tray 2 having an upper end opening portion 21 and a medical device storage portion 22; and a sheet-like lid portion 3 that closes the upper end opening portion 21 of the tray 2. The tray 2 includes an annular flange portion 23 provided on the entire periphery of the upper end opening portion 21.

In the packaging container 1, the sheet-like lid portion 3 is peelably fixed on the annular flange portion 23 and an annular heat seal portion 4 having a rectangular outer edge is provided. The annular heat seal portion 4 includes a first-side seal portion 5 and a second-side seal portion 6, which are opposite to each other, and a third-side seal portion 7 and a fourth-side seal portion 8, which are positioned between the first-side seal portion 5 and the second-side seal portion 6 and opposite to each other.

The sheet-like lid portion 3 includes a flap portion 31 protruding from the first-side seal portion 5 of the annular heat seal portion 4. One end of the third-side seal portion 7 and one end of the fourth-side seal portion 8 are positioned on the second-side seal portion 6 side by a predetermined length with respect to the first-side seal portion 5. The first-side seal portion 5 includes a central seal portion 51, a first side-part seal portion 52 extending obliquely and connecting one end 51a of the central seal portion 51 with one end 71 of the third-side seal portion 7, and a second side-part seal portion 53 extending obliquely and connecting the other end 51b of the central seal portion 51 and one end 81 of the fourth-side seal portion 8.

The first-side seal portion 5 includes a plurality of (in this example, two) central seal extension portions 54 and 55 extending from the outer edge of the central seal portion 51 and separated from each other by a predetermined length, a first side-part seal extension portion 56 extending from the outer edge of the first side-part seal portion 52, and a second side-part seal extension portion 57 extending from the outer edge of the second side-part seal portion 53. The outer edge of a distal end portion of the central seal extension portion 54, the outer edge of a distal end portion of the central seal extension portion 55, the outer edge of a distal end portion of the first side-part seal extension portion 56, and the outer edge of a distal end portion of the second side-part seal extension portion 57 have a rounded shape without corners. Moreover, a distance between the one end 51a and the other end 51b of the central seal portion 51 is 45/100 to 55/100 of a distance between the outer edge of the one end 71 of the third-side seal portion 7 and the outer edge of the one end 81 of the fourth-side seal portion 8.

Furthermore, the packaged medical device according to an embodiment of the present disclosure includes the medical device packaging container 1 described above and a medical device 10 stored in the medical device storage portion 22 of a tray 2, and the upper end opening portion 21 of the tray 2 is peelably sealed by the sheet-like lid portion 3 in a state in which the medical device 10 is stored.

The medical device packaging container 1 includes a tray 2 having the upper end opening portion 21 and the medical device storage portion 22, and the sheet-like lid portion 3 that closes the upper end opening portion 21 of the tray 2.

Furthermore, the packaged medical device includes the medical device packaging container 1 described above and the medical device 10 stored therein.

Figure 4:
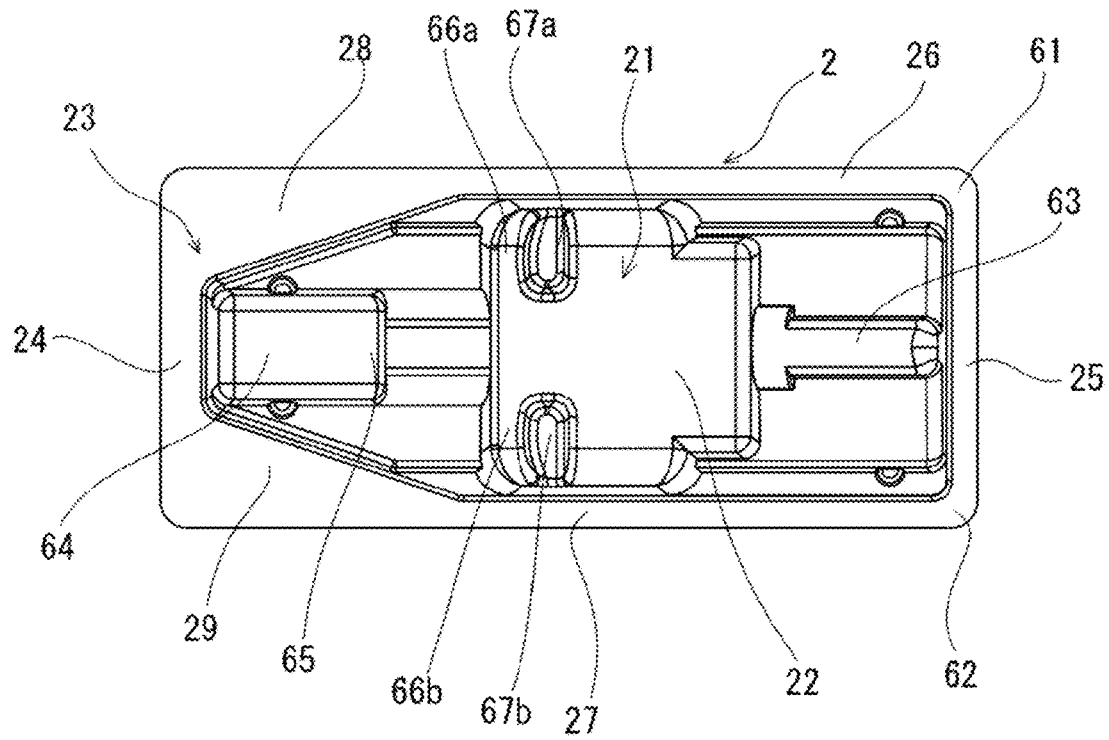
FIG. 4 is a plan view of a tray used for the medical device packaging container and the packaged medical device according to an embodiment of the present disclosure, which are illustrated in FIG. 1.
Figure 5:
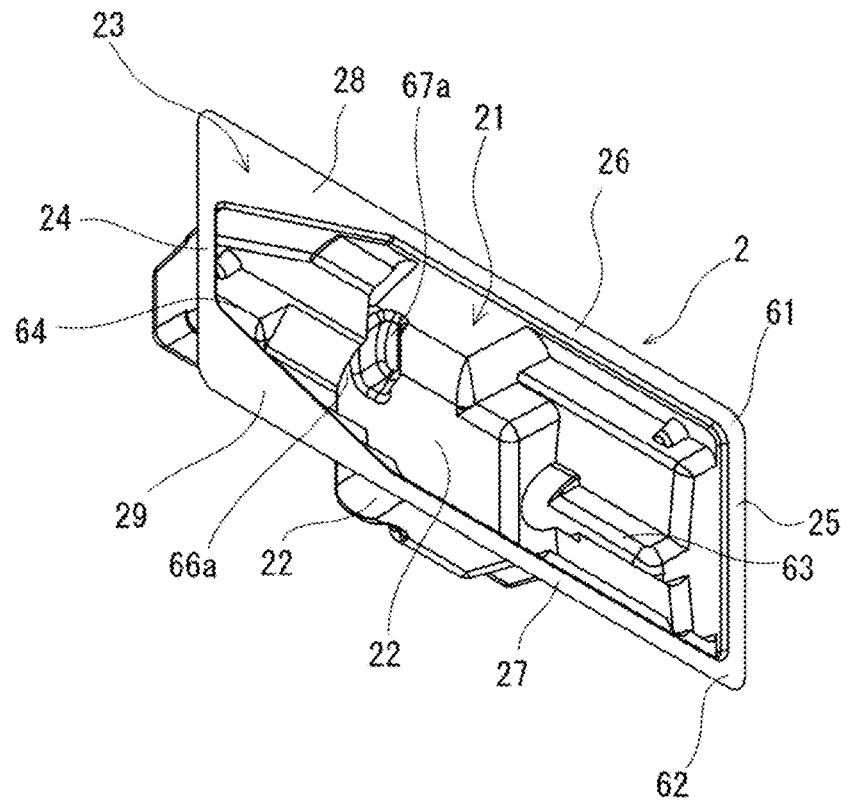
FIG. 5 is a perspective view of a tray used for the medical device packaging container and the packaged medical device according to an embodiment of the present disclosure, which are illustrated in FIG. 1.

As illustrated in FIGS. 4 and 5, the tray 2 includes the upper end opening portion 21, the medical device storage portion 22, and the annular flange portion 23 provided on the entire periphery of the upper end opening portion 21. The annular flange portion 23 has a flat upper surface and is endless. The medical device storage portion 22 forms a recess, and can store the medical device 10 in a state of not protruding as compared with the upper end opening portion 21.

Furthermore, in the tray 2 of this embodiment, the outer edge shape (outer edge shape of the annular flange portion 23) is rectangular in a top view, specifically, the tray 2 has a long rectangular shape. The annular flange portion 23 includes a first-side flange portion 24, a second-side flange portion 25 opposite to the first-side flange portion 24, and a third-side flange portion 26 and a fourth-side flange portion 27, which are positioned between the first-side flange portion 24 and the second-side flange portion 25 and opposite to each other. The first-side flange portion 24 and the second-side flange portion 25 are parallel to each other, and the third-side flange portion 26 and the fourth-side flange portion 27 are parallel to each other. The third-side flange portion 26 and the fourth-side flange portion 27 are orthogonal to the first-side flange portion 24 and the second-side flange portion 25.

In the tray 2 of this embodiment, the first-side flange portion 24 and the second-side flange portion 25 are short-side portions, and the third-side flange portion 26 and the fourth-side flange portion 27 are long-side portions. Note that in the tray 2, the lengths of four flange portions may be substantially equal.

One end of the first-side flange portion 24 and one end of the third-side flange portion 26 are connected to form a first corner flange portion 28. The other end of the first-side flange portion 24 and one end of the fourth-side flange portion 27 are connected to form a second corner flange portion 29. One end of the second-side flange portion 25 and the other end of the third-side flange portion 26 are connected to form a third corner flange portion 61. The other end of the second-side flange portion 25 and the other end of the fourth-side flange portion 27 are connected to form a fourth corner flange portion 62. Outer edges of four corner flange portions 28, 29, 61, and 62 are curved portions and do not have edges.

Furthermore, in the tray 2 of this embodiment, the flange portion of the first corner flange portion 28 and the flange portion of the second corner flange portion 29 have a triangular shape having a corner as a vertex and a base opposite to the corner. The flange portions other than the first corner flange portion 28 and the second corner flange portion 29 are belt-like portions extending with substantially the constant width. The outer edge of the annular flange portion 23 of this embodiment is linear except the corner flange portion. Note that the outer edge of the annular flange portion 23 is not limited to a linear shape, and may have an arc shape, a wavy line shape, or the like.

In the tray 2 of this embodiment, the medical device storage portion 22 includes a recess portion and a protrusion portion, which correspond to the outer shape of the medical device 10 to be stored, and the medical device 10 can be stored therein so as to be substantially immovable. Note that the shape of the medical device storage portion 22 is appropriately changed depending on the medical device to be stored.

As a material of the tray 2, a material capable of forming a heat seal portion is used. Note that only the annular flange portion 23 described above may be heat-sealable.

As the material of the tray 2, it is preferable to have a certain degree of strength and hardness, and for example, a thermoplastic resin such as polyolefin such as polypropylene and polyethylene, a vinyl chloride resin, a polyester resin (specifically, polyethylene terephthalate), or a polystyrene/polypropylene resin can be suitably used, and moreover, a material having a certain degree of transparency is more preferable.

Furthermore, in a case where the medical device to be stored stores a drug susceptible to light, various pigments and ultraviolet absorbers may be contained in the material for forming the tray. Moreover, it is preferable that the resin includes a layer having a thickness of about 30 μm to 70 μm and formed of a resin having low gas permeability and low water vapor permeability (for example, polyvinylidene chloride, an ethylene-vinyl alcohol copolymer, and polyethylene terephthalate). Specifically, a resin (having a gas barrier property) including three layers of polyethylene terephthalate/ethylene-vinyl alcohol copolymer/polypropylene and a resin formed of polypropylene alone are suitable.

Figure 10:
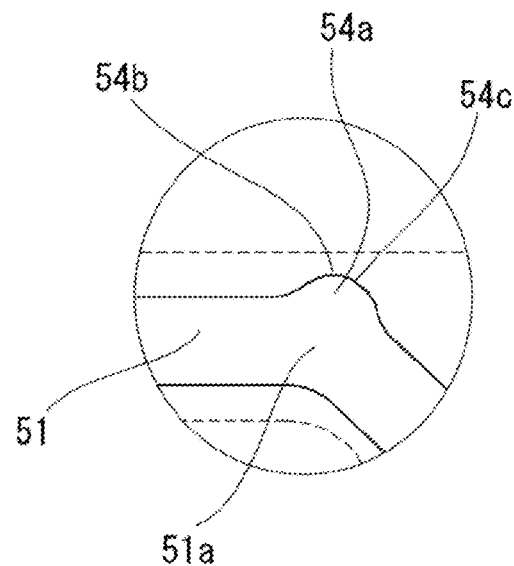
FIG. 10 is an explanatory view for explaining a modification example of a central seal extension portion of a central seal portion of a first-side seal portion of an annular heat seal portion in the medical device packaging container and the packaged medical device according to an embodiment of the present disclosure.

As the sheet-like lid portion 3, one that can be heat-sealed to the annular flange portion of the tray is used. As illustrated in FIGS. 2 and 10, the sheet-like lid portion 3 of this embodiment has a rectangular shape, and a first side and a second side opposite to the first side are short sides, and a third side and a fourth side, which are positioned between the first side and the second side and opposite to each other are long sides.

Figure 6:
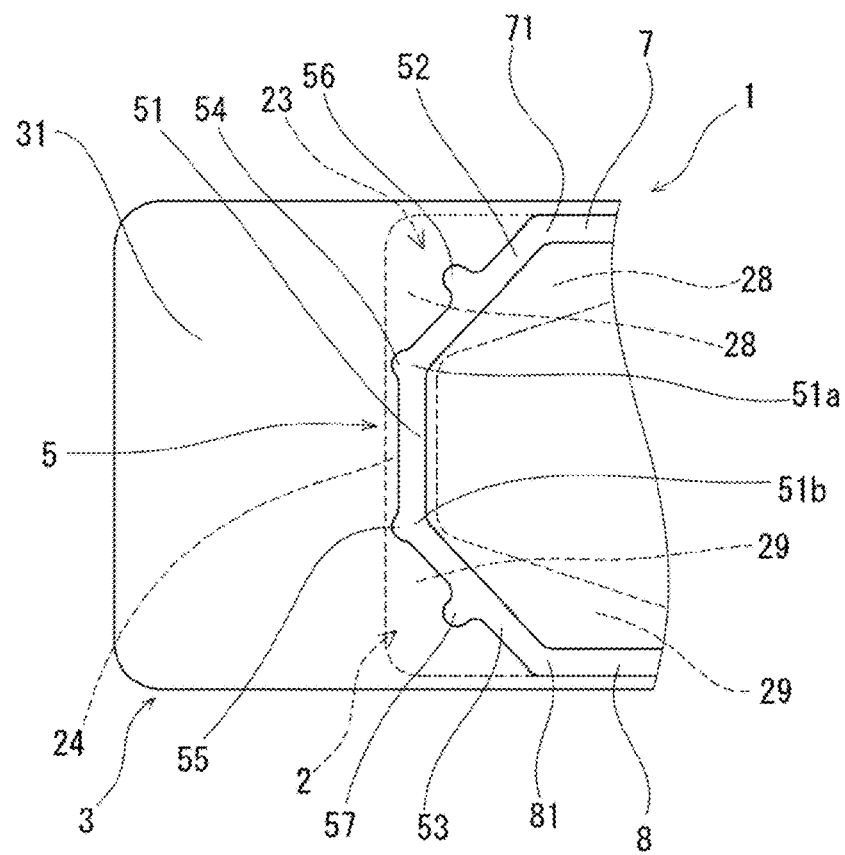
FIG. 6 is an enlarged view of a part near a flap portion of a sheet-like lid portion in the medical device packaging container and the packaged medical device according to an embodiment of the present disclosure, which are illustrated in FIG. 1.
Figure 7:
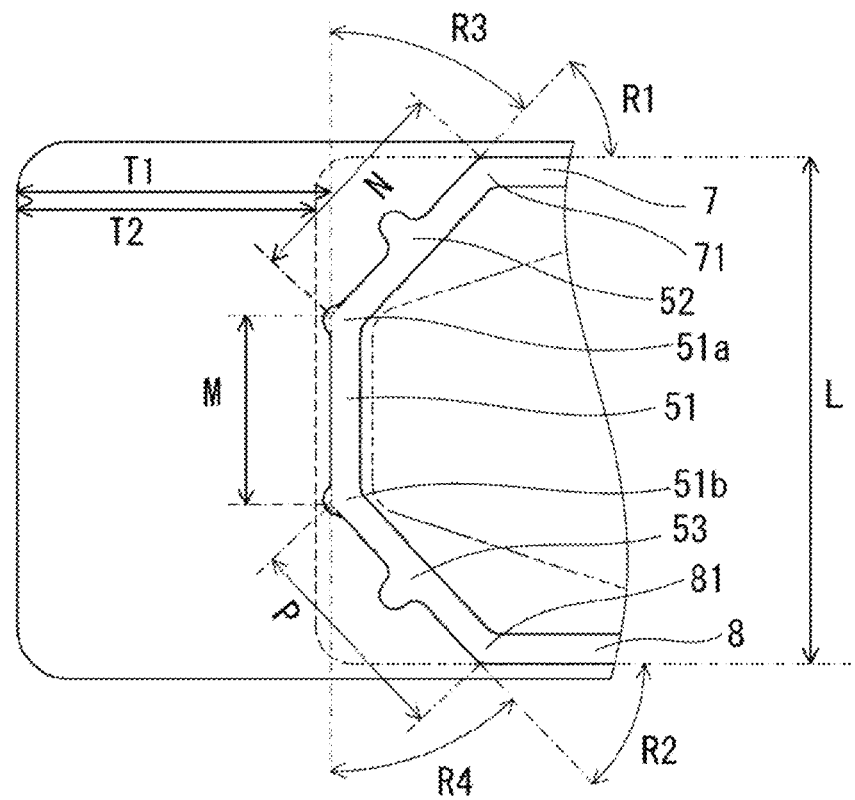
FIG. 7 is an explanatory view for explaining a first-side seal portion of an annular heat seal portion in the medical device packaging container and the packaged medical device according to an embodiment of the present disclosure, which are illustrated in FIG. 1.

As illustrated in FIGS. 2, 6, and 7, the sheet-like lid portion 3 includes the flap portion 31 protruding by a predetermined length from the first-side seal portion 5 of the annular heat seal portion 4 to be described later. The flap portion 31 is used as a grip portion at the time of the peeling-off. Note that the flap portion 31 also protrudes from the first-side flange portion 24 of the tray 2 by a predetermined length.

A distance T1 between one end of a portion of the flap portion 31 extending from the first-side seal portion 5 and the central seal portion 51 of the first-side seal portion 5, and a distance T2 between one end of the portion of the flap portion 31 extending from the first-side seal portion 5 and the first-side flange portion 24 (T1, T2) are preferably 35 mm to 50 mm, and particularly preferably 40 mm to 46 mm.

Furthermore, the distance T1 and the distance T2 are preferably 50/100 to 100/100 of a distance L between the outer edge of one end 71 of the third-side seal portion 7 and the outer edge of one end 81 of the fourth-side seal portion 8, and in particular, the distance T1 and the distance T2 are preferably 50/100 to 70/100 of the distance L, and in particular, preferably 55/100 to 65/100. T1 is preferably longer than T2 by about 3 mm to 10 mm, and in particular, preferably longer by about 4 mm to 8 mm.

Furthermore, the distance L between the outer edge of one end 71 of the third-side seal portion 7 and the outer edge of one end 81 of the fourth-side seal portion 8 and a length on the short-side side of the tray are generally about 50 mm to 80 mm. In a case where the distance L (length on the short-side side of the tray) is in such a range, it is effective that the distance T1 and the distance T2 are in the above-described ranges.

Note that in the tray, the distance L between the outer edge of one end 71 of the third-side seal portion 7 and the outer edge of one end 81 of the fourth-side seal portion 8 (or a length on a short-side side of the tray) may be equal to or less than 40 mm. Because the lengths (distances T1 and T2) of the flap portion 31 protruding from the first-side flange portion 24 of the tray 2 by a predetermined length does not affect the opening strength of the seal, the length can be arbitrarily set depending on the product. For example, in a case where a user having a restriction on the movement of fingers such as a rheumatism patient opens the product, it is effective to set T1 and T2 to be long to some extent in terms of an opening property. In this case, it is desirable that T1 and T2 are set to substantially be equal to the width on the short-side side of the sheet-like lid portion 3. This is for the following reason. The user grips the medical device packaging container 1 with a hand from the bottom side of the tray 2 and uses the medical device packaging container 1. That is, because the width portion on the short-side side of the sheet-like lid portion 3 is gripped by the hand and used, the width is set to such an extent that the width portion can be gripped. Therefore, when T1 and T2 also can be set to be equal to the width on the short-side side of the sheet-like lid portion 3, the gripping can be satisfactorily performed. Note that improvement of the gripping property cannot be expected even when the distances T1 and T2 are longer. Therefore, the maximum protruding length is preferably equal to or substantially equal to the width on the short-side side of the sheet-like lid portion 3 (the distance T1 and the distance T2 are 100/100 of the distance L between the outer edge of one end 71 of the third-side seal portion 7 and the outer edge of one end 81 of the fourth-side seal portion 8). Furthermore, when the length of the flap portion 31 is too short, it is difficult to grip and open the tray. Therefore, when the length is about half the length for gripping the tray with a hand, the flap portion can be sufficiently gripped with fingers. Therefore, as the lower limit, the protruding length of the flap portion is preferably set to half the width of the short side of the flap portion 31 or half the width on the short-side side of the tray (the distance T1 and the distance T2 are about 50/100 of the distance L between the outer edge of one end 71 of the third-side seal portion 7 and the outer edge of one end 81 of the fourth-side seal portion 8).

Furthermore, as illustrated in FIG. 2, the sheet-like lid portion 3 includes a protruding portion 35 protruding over the entire periphery from the outer edge of the tray 2 and from the annular heat seal portion 4. The flange portion 23 of the tray 2 does not exist on the lower surface of the protruding portion 35.

Figure 15:
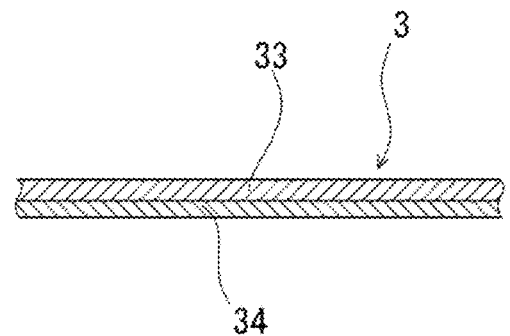
FIG. 15 is a partially enlarged cross-sectional view of the sheet-like lid portion illustrated in FIG. 15.

As illustrated in FIG. 15, the sheet-like lid portion 3 of this embodiment includes a base material layer 33 and an adhesive resin layer 34 provided on the lower surface of the base material layer 33. The adhesive resin layer 34 may be provided on the entire lower surface of the base material layer 33, or may be provided only on a heat seal formation portion of the sheet-like lid portion 3.

As a material for forming the base material layer 33, a sheet formed of polyester, polyolefin such as polypropylene and polyethylene, nylon, polyester such as PET, or a thermoplastic nonwoven sheet made of synthetic resin such as polyethylene and polypropylene is used.

Note that as the sheet-like lid portion 3, a sheet-like lid portion having gas permeability and a sheet-like lid portion having a gas barrier property are selected in consideration of the medical device to be stored or necessity of sterilization. In the case of the sheet-like lid portion having gas permeability, a base material layer having gas permeability such as a synthetic resin nonwoven sheet is used.

Furthermore, in the case of the sheet-like lid portion having a gas barrier property, a gas barrier sheet is selected. The gas barrier sheet suppresses permeation of moisture from the inside of the packaging container or permeation of oxygen from the outside. As the gas barrier sheet, a metal deposition sheet formed by depositing, on the surface thereof, a metal foil formed of aluminum, silver, gold or the like, or aluminum, silver, gold or the like, an inorganic material deposition sheet formed by depositing, on the surface thereof, $SiO_X$ or the like, or a gas barrier resin sheet such as a sheet formed of polyvinylidene chloride, polyvinylidene chloride-polyvinyl chloride, polyvinylidene chloride-acrylic acid ester copolymer, high density polyethylene or the like can be suitably used.

The adhesive resin layer is a layer for peelably heat-sealing the base material layer to the tray 2, and for example, as the adhesive resin layer, an ethylene-vinyl acetate resin, an ethylene-acrylic acid resin, an olefin resin such as a resin formed by blending polypropylene and polyethylene, a two-liquid curable urethane dry laminate adhesive, low melting point polyethylene, or the like can be used.

Furthermore, the sheet-like lid portion 3 may have a surface protective layer on the surface of the base material layer 33. The surface protective layer is formed by coating a synthetic resin, such as polyester, polypropylene, polyethylene, nylon, PET, an epoxy resin, or a polyamide resin, or by bonding the synthetic resin film, paper, or the like.

As illustrated in FIG. 2, the medical device packaging container 1 according to an embodiment of the present disclosure includes the annular heat seal portion 4 for peelably fixing the sheet-like lid portion 3 onto the annular flange portion 23 of the tray 2. The annular heat seal portion 4 of this embodiment is formed in an endless belt-like shape and has a rectangular outer edge.

As illustrated in FIGS. 2 and 6 to 8, the annular heat seal portion 4 includes the first-side seal portion 5 and second-side seal portion 6, which are opposite to each other, and the third-side seal portion 7 and fourth-side seal portion 8, which are positioned between the first-side seal portion 5 and the second-side seal portion 6 and opposite to each other. The third-side seal portion 7 and the fourth-side seal portion 8 are parallel to each other.

In the annular heat seal portion 4 of this embodiment, the first-side seal portion 5 and the second-side seal portion 6 are short-side portions, and the third-side seal portion 7 and the fourth-side seal portion 8 are long-side portions. One end of the third-side seal portion 7 and one end of the fourth-side seal portion 8 are positioned on the second-side side by a predetermined length with respect to the first-side seal portion 5. Note that the first-side seal portion 5, the second-side seal portion 6, the third-side seal portion 7, and the fourth-side seal portion 8 may have substantially the same length.

The first-side seal portion 5 is formed on the first-side flange portion 24, first corner flange portion 28, and second corner flange portion 29 of the tray 2. The second-side seal portion 6 is formed on the second-side flange portion 25, the third-side seal portion 7 is formed on the third-side flange portion 26, and the fourth-side seal portion 8 is formed on the fourth-side flange portion 27.

The first-side seal portion 5 includes a central seal portion 51, a first side-part seal portion 52 extending obliquely and connecting one end 51a of the central seal portion 51 with one end 71 of the third-side seal portion 7, and a second side-part seal portion 53 extending obliquely and connecting the other end 51b of the central seal portion 51 and one end 81 of the fourth-side seal portion 8.

The central seal portion 51 is positioned on the first-side flange portion 24, the first side-part seal portion 52 is positioned on the first corner flange portion 28, and the second side-part seal portion 53 is positioned on the second corner flange portion 29.

The central seal portion 51 is formed on the central portion of the first-side flange portion 24 and has a length shorter than the entire length of the first-side flange portion 24 and a length about half the entire length of the first-side flange portion 24. Furthermore, as illustrated in FIG. 7, the length of the central seal portion 51 (distance M between one end 51a and the other end 51b of the central seal portion 51) is 45/100 to 55/100 of the distance L between the outer edge of one end 71 of the third-side seal portion 7 and the outer edge of one end 81 of the fourth-side seal portion 8. Preferably, the distance M is 47/100 to 53/100 of the distance L.

Furthermore, in the central seal portion 51 of this embodiment, as illustrated in FIGS. 2 and 6, the outer edge of the central seal portion 51, which includes the extension portions 54 and 55 to be described later, does not reach the outer edge of the flange portion 23, and a portion which is not heat sealed (non-heat seal portion) is formed between the outer edge of the flange portion 23 and the outer edge of the central seal portion 51. Furthermore, in the central seal portion 51 of this embodiment, the inner edge of the central seal portion 51 does not reach the inner edge of the flange portion 23, and a portion which is not heat sealed (non-heat seal portion) is formed between the inner edge of the flange portion 23 and the inner edge of the central seal portion 51.

The central seal portion 51 is preferably linear as in this embodiment, but may be curved or wavy.

The central seal portion 51 of the first-side seal portion 5 and the second-side seal portion 6 are parallel to each other. The third-side seal portion 7 and the fourth-side seal portion 8 are parallel to each other. The third-side seal portion 7 and the fourth-side seal portion 8 are orthogonal to the central seal portion 51 of the first-side seal portion 5 and the second-side seal portion 6. As illustrated in FIGS. 2, 6, and 7, the first-side seal portion 5 includes two central seal extension portions 54 and 55 extending from the outer edge of the central seal portion 51 and extending in an outer edge direction of the first-side flange portion 24. The central seal extension portions 54 and 55 are separated by a predetermined length.

The first side-part seal portion 52 of the first-side seal portion 5 extends obliquely so as to connect one end 51a of the central seal portion 51 with one end 71 of the third-side seal portion 7. As illustrated in FIG. 7, an inclination angle R1 of a virtual line connecting one end 51a of the central seal portion 51 with one end 71 of the third-side seal portion 7 with respect to the third-side seal portion 7 is preferably 30 degrees to 60 degrees. In particular, the inclination angle R1 is preferably 40 degrees to 50 degrees.

Similarly, the second side-part seal portion 53 of the first-side seal portion 5 extends obliquely so as to connect the other end 51b of the central seal portion 51 with one end 81 of the fourth-side seal portion 8. As illustrated in FIG. 7, an inclination angle R2 of a virtual line connecting the other end 51b of the central seal portion 51 with one end 81 of the fourth-side seal portion 8 with respect to the fourth-side seal portion 7 is preferably 30 degrees to 60 degrees. In particular, the inclination angle R2 is preferably 40 degrees to 50 degrees.

Furthermore, as illustrated in FIG. 7, an inclination angle R3 of a virtual line connecting one end 51a of the central seal portion 51 with one end 71 of the third-side seal portion 7 with respect to the central seal portion 51 is preferably 30 degrees to 60 degrees. In particular, the inclination angle R3 is preferably 40 degrees to 50 degrees. Similarly, an inclination angle R4 of a virtual line connecting the other end 51b of the central seal portion 51 with one end 81 of the fourth-side seal portion 8 with respect to the central seal portion 51 is preferably 30 degrees to 60 degrees. In particular, the inclination angle R4 is preferably 40 degrees to 50 degrees.

A length N of the first side-part seal portion 52 (distance between one end 51a of the central seal portion 51 and one end 71 of the third-side seal portion 7) is preferably substantially equal to the distance M (length of the central seal portion 51) between one end 51a and the other end 51b of the central seal portion 51. Specifically, the length N of the first side-part seal portion 52 is preferably 90/100 to 110/100 of a length M of the central seal portion 51, and particularly preferably 95/100 to 105/100 of the length M of the central seal portion 51.

A length P of the second side-part seal portion 53 (distance between the other end 51b of the central seal portion 51 and one end 81 of the fourth-side seal portion 8) is preferably substantially equal to the distance M (length of the central seal portion 51) between one end 51a and the other end 51b of the central seal portion 51. Specifically, the length P of the second side-part seal portion 53 is preferably 90/100 to 110/100 of the length M of the central seal portion 51, and particularly preferably 95/100 to 105/100 of the length M of the central seal portion 51.

Furthermore, the length P of the second side-part seal portion 53 is preferably substantially equal to the length N of the first side-part seal portion 52. Specifically, the length P of the second side-part seal portion 53 is preferably 90/100 to 110/100 of the length N of the first side-part seal portion 52, and particularly preferably 95/100 to 105/100 of the length N of the first side-part seal portion 52.

The distance between one end 51a and the other end 51b of the central seal portion 51 is preferably substantially equal to the distance between one end 51a of the central seal portion 51 and one end 71 of the third-side seal portion 7.

The first side-part seal portion 52 and the second side-part seal portion 53 are preferably linear as in this embodiment, but may be curved or wavy.

As illustrated in FIGS. 2, 6, and 7, the first-side seal portion 5 includes two central seal extension portions 54 and 55 extending from the outer edge of the central seal portion 51 and extending in the outer edge direction of the first-side flange portion 24. The central seal extension portions 54 and 55 are separated by a predetermined length.

The central seal extension portion 54 of this embodiment is formed at a connecting portion (corner portion) between one end 51a of the central seal portion 51 and the first side-part seal portion 52, and the central seal extension portion 55 is formed at a connecting portion (corner portion) between the other end 51b of the central seal portion 51 and the second side-part seal portion 53. Therefore, the central seal extension portions 54 and 55 partially extend from the central seal portion 51, and partially extend from the first side-part seal portion 52 or the second side-part seal portion 53.

A separation distance between the central seal extension portions 54 and 55 is preferably 27 mm to 39 mm, and particularly preferably 30 mm to 35 mm.

Figure 11:
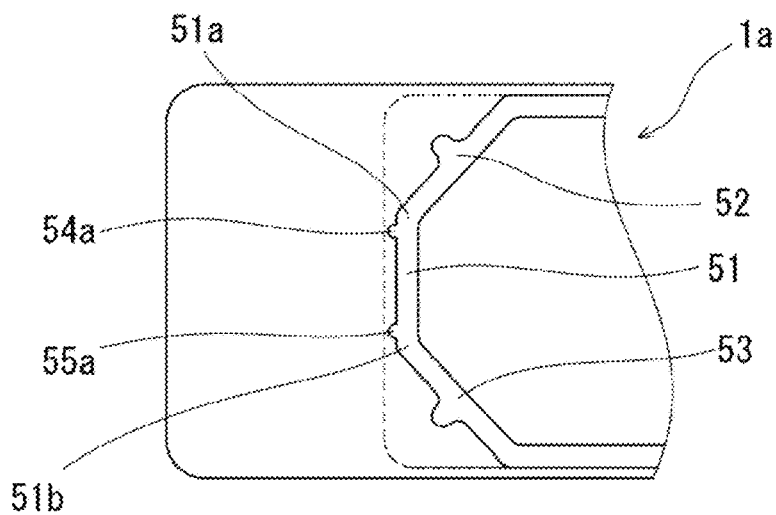
FIG. 11 is an explanatory view for explaining a modification example of a first-side seal portion of an annular heat seal portion in the medical device packaging container and the packaged medical device according to an embodiment of the present disclosure.

Furthermore, as in a medical device packaging container 1a of an embodiment illustrated in FIG. 11, central seal extension portions 54a and 55a may be provided in the central seal portion 51 itself instead of the connecting portion (corner portion) between one end 51a of the central seal portion 51 and the first side-part seal portion 52 and the connecting portion (corner portion) between the other end 51b of the central seal portion 51 and the second side-part seal portion 53. In this case, it is preferable that the central seal extension portions 54a and 55a are provided at positions slightly close to the central side with respect to opposite end portions of the central seal portion 51.

Figure 12:
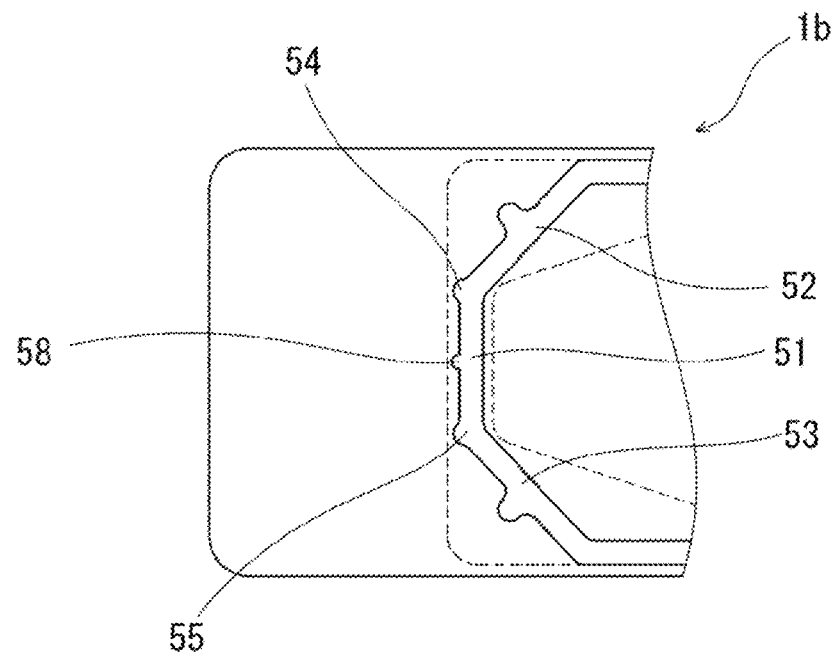
FIG. 12 is an explanatory view for explaining a modification example of a first-side seal portion of an annular heat seal portion in the medical device packaging container and the packaged medical device according to an embodiment of the present disclosure.

Moreover, the number of the central seal extension portions is not limited to two as in the above-described embodiment, and a third central seal extension portion 58 may be provided as in a medical device packaging container 1b of an embodiment illustrated in FIG. 12. In this case, the third central seal portion 58 is preferably positioned in the middle between the central seal extension portions 54 and 55. Furthermore, the number of the central seal extension portions is preferably two to five, and particularly preferably two or three.

The outer edge of a distal end portion of the central seal extension portion 54 and the outer edge of a distal end portion of the central seal extension portion 55 have a rounded shape without corners. Furthermore, in the central seal extension portions 54 and 55 of this embodiment, the outer edges of the extension portions entirely have a rounded shape without corners. Moreover, in the central seal extension portions 54 and 55 of this embodiment, the outer edges are all formed to have a curved portion and do not have a straight portion. Such a configuration is preferable, but the central seal extension portions 54 and 55 may have straight portions 54b and 54c as in the extension portion 54a illustrated in FIG. 10.

Furthermore, the central seal extension portions 54 and 55 are not limited to those having a partial circular shape (fan shape, crescent shape) as in this embodiment, and may have a triangular shape, a rectangular shape, or a polygonal shape as long as the outer edge of the distal end portion has a rounded shape without corners.

As illustrated in FIGS. 2 and 6 to 8, the first-side seal portion 5 includes the first side-part seal extension portion 56 extending from the outer edge of the first side-part seal portion 52, and the second side-part seal extension portion 57 extending from the outer edge of the second side-part seal portion 53. As illustrated in FIGS. 2 and 6 to 8, the first side-part seal extension portion 56 is formed at the central portion of the first side-part seal portion 52, and the second side-part seal extension portion 57 is formed at the central portion of the second side-part seal portion 53.

Figure 9:
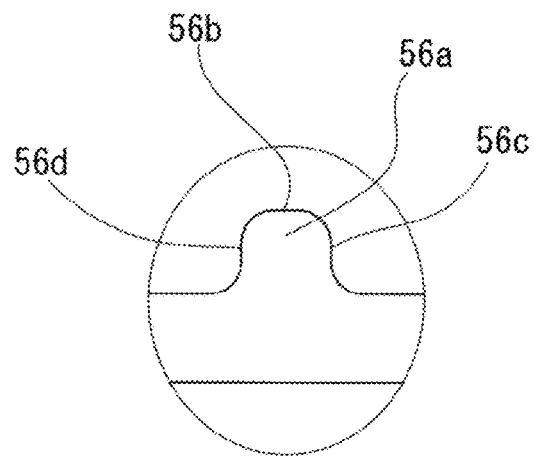
FIG. 9 is an explanatory view for explaining a modification example of a side-part seal extension portion of a side-part seal portion of a first-side seal portion of an annular heat seal portion in the medical device packaging container and the packaged medical device according to an embodiment of the present disclosure.

The outer edge of a distal end portion of the first side-part seal extension portion 56, and the outer edge of a distal end portion of the second side-part seal extension portion 57 have a rounded shape without corners. In this embodiment, in the first side-part seal extension portion 56 and the second side-part seal extension portion 57, the outer edges of the extension portions entirely have a rounded shape without corners. Moreover, in this embodiment, in the first side-part seal extension portion 56 and the second side-part seal extension portion 57, the outer edges are all formed to have a curved portion and do not have a straight portion. Such a configuration is preferable, but the first side-part seal extension portion 56 and the second side-part seal extension portion 57 may have straight portions 56b, 56c, and 56d as in an extension portion 56a illustrated in FIG. 9.

Furthermore, the first side-part seal extension portion 56 and the second side-part seal extension portion 57 are not limited to those having a rectangular shape as in this embodiment, and may have a partial circular shape (for example, a fan shape, a semicircular shape, and a crescent shape), a triangular shape, or a polygonal shape as long as the outer edge of the distal end portion has a rounded shape without corners.

Figure 8:
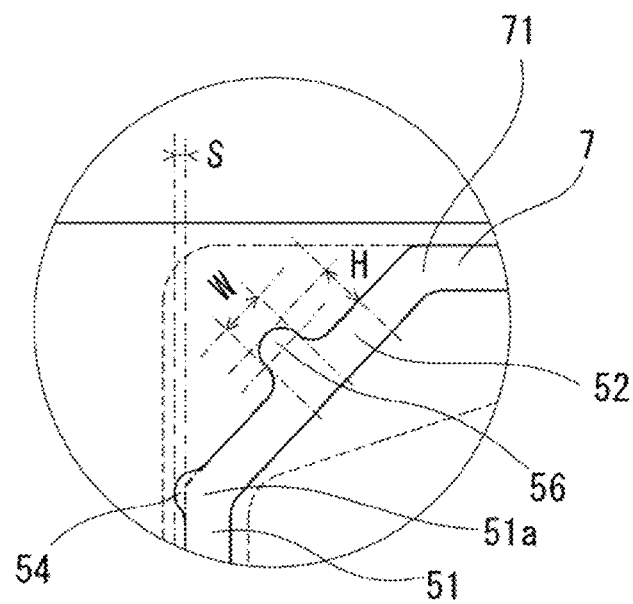
FIG. 8 is an explanatory view for explaining a side-part seal portion of a first-side seal portion of an annular heat seal portion in the medical device packaging container and the packaged medical device according to an embodiment of the present disclosure, which are illustrated in FIG. 1.

Furthermore, as illustrated in FIG. 8, an extension length H of the first side-part seal extension portion 56 and an extension length H of the second side-part seal extension portion 57 are preferably 2 mm to 5 mm, and particularly preferably 3 mm to 4 mm. Furthermore, a width W of the central portion of the first side-part seal extension portion 56 and a width W of the central portion of the second side-part seal extension portion 57 are preferably 2 mm to 5 mm, and particularly preferably 3 mm to 4 mm.

As illustrated in FIG. 2, the outer edge of the second-side seal portion 6 and the outer edge of the second-side flange portion 25 of the tray 2 substantially coincide with each other. A portion which is not heat sealed (non-heat seal portion) is formed between the inner edge of the second-side seal portion 6 and the inner edge of the second-side flange portion 25 of the tray 2. The outer edge of the third-side seal portion 7 and the outer edge of the third-side flange portion 26 of the tray 2 substantially coincide with each other. A portion that is not heat sealed (non-heat seal portion) is formed between the inner edge of the third-side seal portion 7 and the inner edge of the third-side flange portion 26 of the tray 2. Similarly, the outer edge of the fourth-side seal portion 8 and the outer edge of the fourth-side flange portion 27 of the tray 2 substantially coincide with each other. A portion which is not heat sealed (non-heat seal portion) is formed between the inner edge of the fourth-side seal portion 8 and the inner edge of the fourth-side flange portion 27 of the tray 2.

The seal width of the annular heat seal portion 4 is preferably constant and 2 mm to 5 mm except for the central seal extension portions 54 and 55, the first side-part seal extension portion 56, and the second side-part seal extension portion 57. In particular, 3 mm to 5 mm is preferable. Note that the seal width may be only required to be substantially constant, and may vary by equal to or less than 2 mm. The variation in the seal width is preferably equal to or less than 1 mm.

Specifically, the width of the central seal portion 51, the width of the first side-part seal portion 52, the width of the second side-part seal portion 53, the width of the second-side seal portion 6, the width of the third-side seal portion 7, and the width of the fourth-side seal portion 8 are preferably 2 mm to 5 mm. Furthermore, the width of the central seal portion 51, the width of the first side-part seal portion 52, the width of the second side-part seal portion 53, the width of the second-side seal portion 6, the width of the third-side seal portion 7, and the width of the fourth-side seal portion 8 are preferably equal to each other.

As formation conditions of the annular heat seal portion 4, the heat-seal temperature differs depending on the material for forming the tray and sheet-like lid portion to be used, but the formation conditions are preferably 110° C. to 130° C., 1 second to 3 seconds, and 4 kgf/cm$^2$ to 6 kgf/cm$^2$.

Figure 13:
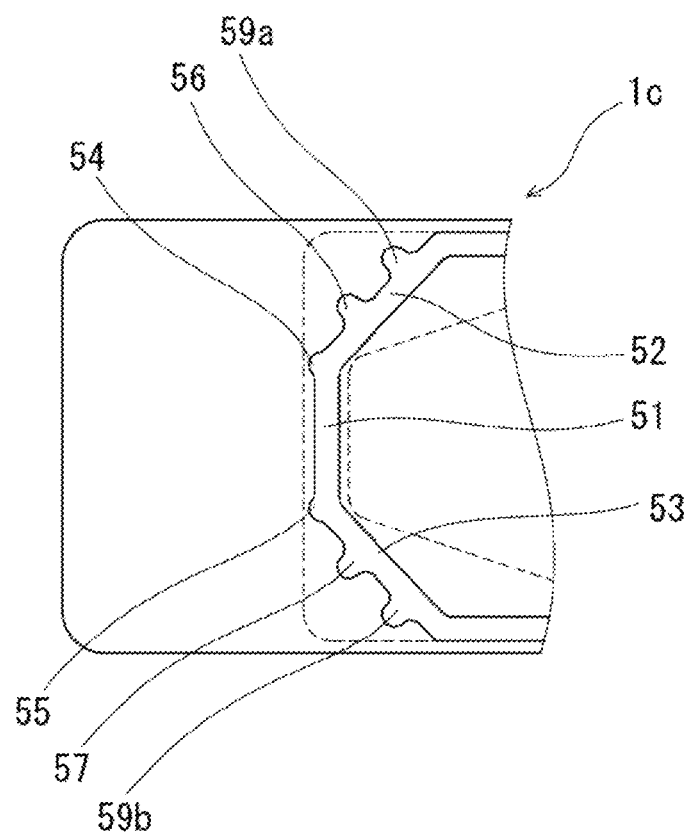
FIG. 13 is an explanatory view for explaining a modification example of a first-side seal portion of an annular heat seal portion in the medical device packaging container and the packaged medical device according to an embodiment of the present disclosure.
Figure 14:
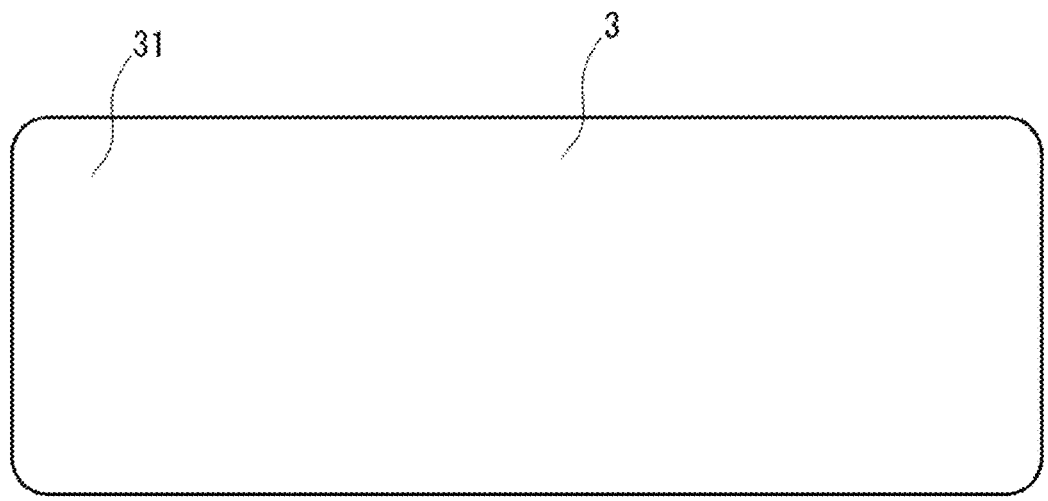
FIG. 14 is a plan view of a sheet-like lid portion used for the medical device packaging container and the packaged medical device according to an embodiment of the present disclosure, which are illustrated in FIG. 1.

Furthermore, as in a medical device packaging container 1c of the embodiment illustrated in FIG. 13, the first side-part seal portion 52 may include a first first-side-part seal extension portion 56 and a second first-side-part seal extension portion 59a, and the two extension portions are provided separated from each other by a predetermined distance. Similarly, the second side-part seal portion 53 may include a first second-side-part seal extension portion 57 and a second second-side-part seal extension portion 59b, and the two extension portions are provided separated from each other by a predetermined distance.

The packaged medical device according to an embodiment of the present disclosure includes the medical device packaging container 1 described above and a medical device 10 stored in the medical device storage portion 22 of the tray 2, and the upper end opening portion 21 of the tray 2 is peelably sealed by the sheet-like lid portion 3 in a state in which the medical device 10 is stored.

Figure 16:
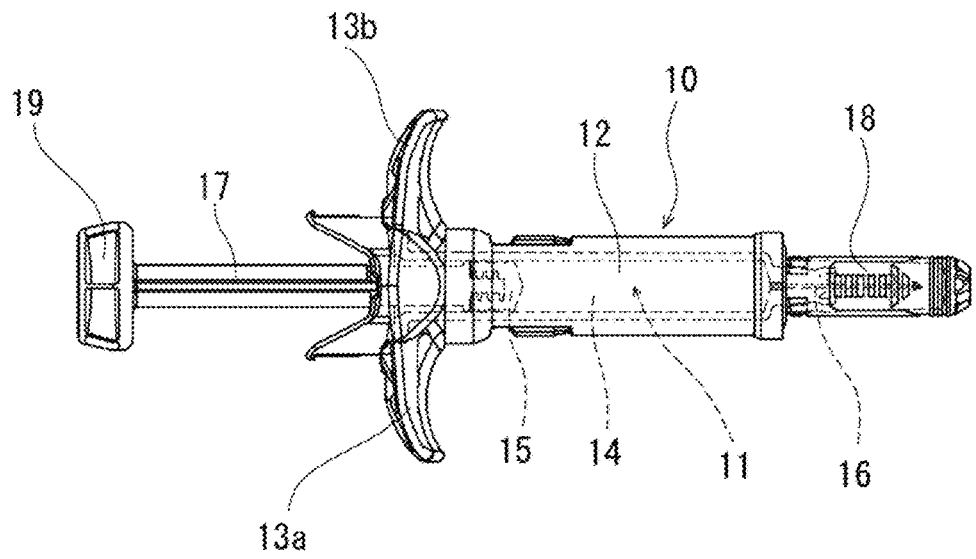
FIG. 16 is a plan view of a medical device used for the medical device packaging container and the packaged medical device according to an embodiment of the present disclosure, which are illustrated in FIG. 1.
Figure 17:
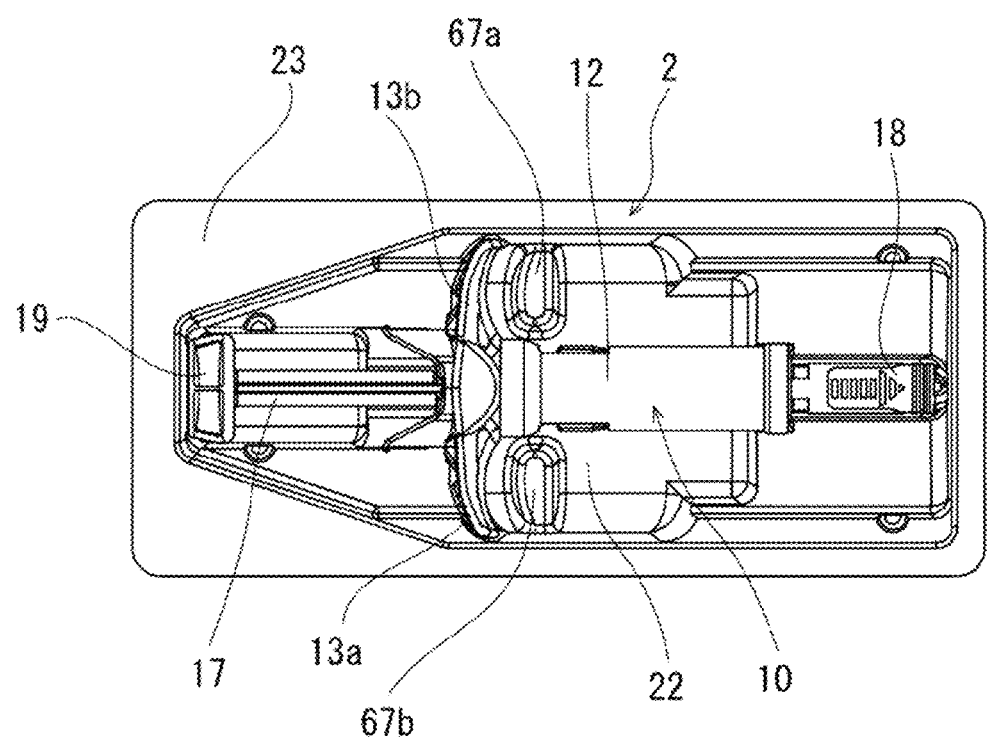
FIG. 17 is an explanatory view for explaining a state in which a medical device is stored in a tray of the medical device packaging container and the packaged medical device according to an embodiment of the present disclosure, which are illustrated in FIG. 1.

As illustrated in FIGS. 1, 2, and 17, the medical device 10 may be of any type as long as the medical device 10 can be stored in the tray 2 and sealed by the sheet-like lid portion 3. In this embodiment, a prefilled syringe as illustrated in FIG. 16 is used as the medical device 10, and in particular, a self-administration prefilled syringe is used as the prefilled syringe of this embodiment. Many self-administration prefilled syringes have an administration assisting function.

A self-administration prefilled syringe 10 includes a main body 12 having an administration assisting function and a prefilled syringe 11 housed in the main body 12.

The prefilled syringe 11 includes an outer cylinder 14, a gasket 15 that is slidably housed in the outer cylinder 14, a plunger 17 that is attached to the gasket, an injection needle 16 that is fixed to a distal end of the outer cylinder 14, and a drug that is stored in a space formed by the outer cylinder 14 and the gasket 15.

Examples of the drug include an antirheumatic drug, a protein preparation, an antibody preparation, hyaluronic acid, an antibacterial drug, an antiviral drug, a vaccine, an antitumor drug, an immunosuppressive drug, a steroid drug, an anti-inflammatory drug, an arthritis therapeutic drug, an antihistamine, an antiallergic drug, a diabetes therapeutic drug, a hormone agent for growth hormone, a bone calcium metabolic drug, a vitamin, a blood preparation, a hematopoietic drug, an antithrombotic drug, an antihyperlipidemic drug, an antiarrhythmic drug, a vasodilator drug, a prostaglandin, a calcium antagonist, an ACE inhibitor, a β-blocker, an antihypertensive drug, a diuretic, a xanthine derivative, a β-agonist, an antiasthmatic drug, an expectorant, an anticholinergic drug, an antidiarrhoeal drug, an antiacid and digestive drug, an antiulcer drug, a purgative drug, a sleeping drug, a sedative drug, an antipyretic drug, a cold drug, an antiepileptic drug, an antipsychotic drug, an antidepressant drug, an antianxiety drug, a central nervous system stimulant drug, a parasympathomimetic drug, sympathomimetic drug, an antiemetic drug, a central excitatory drug, an anti-parkinsonian drug, a muscle relaxant drug, an antispasmodic drug, an anesthetic drug, an antipruritic drug, an antimigraine drug, an oligonucleotide, and a genetic disease drug.

Furthermore, as illustrated in FIG. 16, the self-administration prefilled syringe 10 includes an injection needle cap 18 on the front side of the main body 12, two finger hook portions 13a and 13b on the rear side of the main body, and a press portion 19 at the rear end of the plunger 17. As illustrated in FIGS. 4, 5, and 17, in order to house the self-administration prefilled syringe 10, the tray 2 of this embodiment includes a main body storage portion at the center, a cap storage portion 63 on the front side of the main body storage portion (on the flange 25 side), on the rear side of the main body storage portion (on the flange 24 side), two raised portions 67a and 67b that restrict the movement of two finger hook portions, two finger hook portion storage portions 66a and 66b, a plunger storage portion 65, and a press portion storage portion 64.

The movement of the self-administration prefilled syringe 10 in a cap direction is restricted by two raised portions 67a and 67b, and the movement of the self-administration prefilled syringe 10 in a press portion direction is restricted by the rear portions (surfaces facing the raised portions) of two finger hook portion storage portions 66a and 66b. As a result, the self-administration prefilled syringe 10 is stored in the tray 2 in a substantially immovable manner. Furthermore, the self-administration prefilled syringe 10 is taken out from the tray 2 by gripping the main body of the self-administration prefilled syringe 10 in the main body storage portion.

Next, with reference to FIGS. 2 and 4, actions of the medical device packaging container and packaged medical device according to embodiments of the present disclosure will be described.

In the medical device packaging container 1 and the packaged medical device according to embodiments of the present disclosure, as described above, the central seal extension portions 54 and 55, the first side-part seal extension portion 56, and the second side-part seal extension portion 57 have the distal end portions of which the outer edges have the rounded shape without corners, and do not have the corners (edges) on which stress tends to concentrate. Therefore, unexpected peeling-off of the heat seal portion due to transportation, dropping, or the like hardly occurs. According to this, a packaged medical device in a good sealed state is provided.

At the time of use, the operator grips and peels off the flap portion 31 of the sheet-like lid portion 3. In a case where the operator grips the central portion on the short-side side of the flap portion 31 of the sheet-like lid portion 3 and pulls the flap portion in a direction substantially parallel to the longitudinal direction of the tray, the peeling-off is started from the central seal extension portions 54 and 55. The distal ends of the central seal extension portions 54 and 55 can be easily peeled off from the central seal portion 51, and function as a good peeling start portion. Following the peeling-off of the central seal extension portions 54 and 55, the central seal portion 51, the first side-part seal portion 52, and the second side-part seal portion 53 are peeled off, and subsequently, the third-side seal portion 7 and the fourth-side seal portion 8 are peeled off. As a result, the medical device 10 stored in the tray 2 can be taken out. In a case where it is desired to completely peel off the sheet-like lid portion 3 from the tray 2, the second-side seal portion 6 is peeled off.

Furthermore, in a case where the operator grips the vicinity of one corner of the flap portion 31 of the sheet-like lid portion and obliquely pulls the flap portion in the longitudinal direction of the tray 2, specifically, in a case where the flap portion is pulled in a direction from the first corner flange portion 28 of the tray 2 toward the fourth corner flange portion 62, the peeling-off is started from the first side-part seal extension portion 56. The distal end of the first side-part seal extension portion 56 can be easily peeled off from the first side-part seal portion 52, and function as a good peeling start portion. Following the peeling-off of the first side-part seal extension portion 56, the first side-part seal portion 52, the central seal portion 51, the third-side seal portion 7, the second side-part seal portion 53, and the fourth-side seal portion 8 are peeled off. As a result, the medical device 10 stored in the tray 2 can be taken out. In a case where it is desired to completely peel off the sheet-like lid portion 3 from the tray 2, the annular heat seal portion 4 entirely is peeled off.

Furthermore, in a case where the operator grips the vicinity of the other corner of the flap portion 31 of the sheet-like lid portion 3 and obliquely pulls the flap portion in the longitudinal direction of the tray 2, specifically, in a case where the flap portion is pulled in a direction from the second corner flange portion 29 of the tray 2 toward the third corner flange portion 61, the peeling-off is started from the second side-part seal extension portion 57. The distal end of the second side-part seal extension portion 57 can be easily peeled off from the second side-part seal portion 53, and function as a good peeling start portion. Following the peeling-off of the second side-part seal extension portion 57, the second side-part seal portion 53, the central seal portion 51, the fourth-side seal portion 8, the first side-part seal portion 52, and the third-side seal portion 7 are peeled off. As a result, the medical device 10 stored in the tray 2 can be taken out. In a case where it is desired to completely peel off the sheet-like lid portion 3 from the tray 2, the annular heat seal portion 4 is entirely peeled off.

The medical device packaging container according to an embodiment of the present disclosure is as follows.

(1) A medical device packaging container including: a tray having an upper end opening portion and a medical device storage portion; and a sheet-like lid portion that closes the upper end opening portion of the tray, in which the tray includes an annular flange portion provided on an entire periphery of the upper end opening portion, the packaging container includes an annular heat seal portion that peelably fixes the sheet-like lid portion on the annular flange portion and has a rectangular outer edge, the annular heat seal portion includes a first-side seal portion and a second-side seal portion, which are opposite to each other, and a third-side seal portion and a fourth-side seal portion, which are positioned between the first-side seal portion and the second-side seal portion and opposite to each other, the sheet-like lid portion includes a flap portion protruding from the first-side seal portion of the annular heat seal portion, one end of the third-side seal portion and one end of the fourth-side seal portion are positioned on the second-side seal portion side by a predetermined length with respect to the first-side seal portion, the first-side seal portion includes a central seal portion, a first side-part seal portion extending obliquely and connecting one end of the central seal portion with the one end of the third-side seal portion, and a second side-part seal portion extending obliquely and connecting the other end of the central seal portion and the one end of the fourth-side seal portion, the first-side seal portion includes two central seal extension portions extending from an outer edge of the central seal portion and separated from each other by a predetermined length, a first side-part seal extension portion extending from an outer edge of the first side-part seal portion, and a second side-part seal extension portion extending from an outer edge of the second side-part seal portion, an outer edge of a distal end portion of the central seal extension portion, an outer edge of a distal end portion of the first side-part seal extension portion, and an outer edge of a distal end portion of the second side-part seal extension portion have a rounded shape without corners, and a distance between the one end and the other end of the central seal portion is 45/100 to 55/100 of a distance between an outer edge of the one end of the third-side seal portion and an outer edge of the one end of the fourth-side seal portion.

In this medical device packaging container, the first-side seal portion includes two central seal extension portions extending from the outer edge of the central seal portion and separated from each other by a predetermined length, the first side-part seal extension portion extending from the outer edge of the first side-part seal portion, and the second side-part seal extension portion extending from the outer edge of the second side-part seal portion, and the distance between the one end and the other end of the central seal portion is 45/100 to 55/100 of the distance between the outer edge of the one end of the third-side seal portion and the outer edge of the one end of the fourth-side seal portion.

Therefore, the sheet-like lid portion can be satisfactorily peeled off from the tray in a case where the flap portion of the sheet-like lid portion is gripped and pulled in a direction parallel to the longitudinal direction of the tray, in a case where the flap portion is pulled obliquely in the longitudinal direction of the tray from the first corner portion of the tray close to the peeling start portion, and in a case where the flap portion is pulled obliquely in the longitudinal direction of the tray from a second corner portion opposite to the first corner portion of the tray and close to the peeling start portion.

Furthermore, because the outer edge of the distal end portion of the central seal extension portion, the outer edge of the distal end portion of the first side-part seal extension portion, and the outer edge of the distal end portion of the second side-part seal extension portion have a rounded shape without corners, the first-side seal portion does not have a so-called seal fragility portion. Therefore, unintended peeling-off of the heat seal portion is unlikely to occur.

Furthermore, the above-described embodiment may be as follows.

(2) The medical device packaging container according to (1), in which the first-side seal portion and the second-side seal portion are short-side portions, and the third-side seal portion and the fourth-side seal portion are long-side portions.

(3) The medical device packaging container according to (1) or (2), in which the third-side seal portion and the fourth-side seal portion are parallel to each other.

(4) The medical device packaging container according to any one of (1) to (3), in which the third-side seal portion and the fourth-side seal portion are orthogonal to the central seal portion of the first-side seal portion and the second-side seal portion.

(5) The medical device packaging container according to any one of (1) to (4), in which an inclination angle of a virtual line connecting the one end of the central seal portion with the one end of the third-side seal portion with respect to the third-side seal portion is from 30 degrees to 60 degrees.

(6) The medical device packaging container according to any one of (1) to (5), in which an inclination angle of a virtual line connecting the other end of the central seal portion with the one end of the fourth-side seal portion with respect to the fourth-side seal portion is from 30 degrees to 60 degrees.

(7) The medical device packaging container according to any one of (1) to (6), in which a distance between the one end and the other end of the central seal portion is substantially equal to a distance between the one end of the central seal portion and the one end of the third-side seal portion.

(8) The medical device packaging container according to any one of (1) to (7), in which a distance between the one end and the other end of the central seal portion is substantially equal to a distance between the other end of the central seal portion and the one end of the fourth-side seal portion.

(9) The medical device packaging container according to any one of (1) to (8), in which a length of the central seal portion is substantially equal to a length of the first side-part seal portion and a length of the second side-part seal portion.

(10) The medical device packaging container according to any one of (1) to (9), in which a seal width of the annular heat seal portion is constant except for the central seal extension portion, the first side-part seal extension portion, and the second side-part seal extension portion.

(11) The medical device packaging container according to any one of (1) to (10), in which a seal width of the annular heat seal portion is constant and is from 2 mm to 5 mm except for the central seal extension portion, the first side-part seal extension portion, and the second side-part seal extension portion.

Furthermore, the medical device according to an embodiment of the present disclosure is as follows.

(12) A packaged medical device including: the medical device packaging container according to any one of (1) to (11); and a medical device stored in the medical device storage portion of the tray, in which the upper end opening portion of the tray is peelably sealed by the sheet-like lid portion in a state in which the medical device is stored.

Furthermore, the above-described embodiment may be as follows.

(13) The packaged medical device according to (12), in which the medical device is a self-administration prefilled syringe.

The invention claimed is:

1. A medical device packaging container comprising:
a tray having an upper end opening portion and a medical device storage portion; and
a sheet-like lid portion that closes the upper end opening portion of the tray; wherein:
the tray comprises an annular flange portion located at an entire periphery of the upper end opening portion;
the packaging container comprises an annular heat seal portion that peelably fixes the sheet-like lid portion on the annular flange portion and has a rectangular outer edge;
the annular heat seal portion comprises a first-side seal portion and a second-side seal portion, which are opposite to each other, and a third-side seal portion and a fourth-side seal portion, which are positioned between the first-side seal portion and the second-side seal portion and opposite to each other;
the sheet-like lid portion comprises a flap portion protruding from the first-side seal portion of the annular heat seal portion;
a first end of the third-side seal portion and a first end of the fourth-side seal portion are positioned on a second-side seal portion side by a predetermined length with respect to the first-side seal portion;
the first-side seal portion includes a central seal portion, a first side-part seal portion extending obliquely and connecting a first end of the central seal portion with the first end of the third-side seal portion, and a second side-part seal portion extending obliquely and connecting a second end of the central seal portion with the first end of the fourth-side seal portion;
the first-side seal portion includes a plurality of central seal extension portions extending from an outer edge of the central seal portion and separated from each other by a predetermined length, a first side-part seal extension portion extending from an outer edge of the first side-part seal portion, and a second side-part seal extension portion extending from an outer edge of the second side-part seal portion;
an outer edge of a distal end portion of each central seal extension portion, an outer edge of a distal end portion of the first side-part seal extension portion, and an outer edge of a distal end portion of the second side-part seal extension portion have a rounded shape without corners; and
a distance between the first end and the second end of the central seal portion is in a range from 45/100 to 55/100 of a distance between an outer edge of the first end of the third-side seal portion and an outer edge of the first end of the fourth-side seal portion.

2. The medical device packaging container according to claim 1, wherein lengths of the first-side seal portion and the second-side seal portion are less than lengths of the third-side seal portion and the fourth-side seal portion.

3. The medical device packaging container according to claim 1, wherein the third-side seal portion and the fourth-side seal portion are parallel to each other.

4. The medical device packaging container according to claim 1, wherein the third-side seal portion and the fourth-side seal portion are orthogonal to the central seal portion and the second-side seal portion.

5. The medical device packaging container according to claim 1, wherein an inclination angle of a virtual line connecting the first end of the central seal portion with the first end of the third-side seal portion with respect to the third-side seal portion is in a range from 30 degrees to 60 degrees.

6. The medical device packaging container according to claim 5, wherein an inclination angle of a virtual line connecting the second end of the central seal portion with the first end of the fourth-side seal portion with respect to the fourth-side seal portion is in a range from 30 degrees to 60 degrees.

7. The medical device packaging container according to claim 1, wherein a distance between the first end and the second end of the central seal portion is substantially equal to a distance between the first end of the central seal portion and the first end of the third-side seal portion.

8. The medical device packaging container according to claim 7, wherein a distance between the first end and the second end of the central seal portion is substantially equal to a distance between the second end of the central seal portion and the first end of the fourth-side seal portion.

9. The medical device packaging container according to claim 1, wherein a length of the central seal portion is substantially equal to a length of the first side-part seal portion and a length of the second side-part seal portion.

10. The medical device packaging container according to claim 1, wherein a seal width of the annular heat seal portion is constant except for the central seal extension portions, the first side-part seal extension portion, and the second side-part seal extension portion.

11. The medical device packaging container according to claim 1, wherein a seal width of the annular heat seal portion is constant and is in a range from 2 mm to 5 mm except for the central seal extension portions, the first side-part seal extension portion, and the second side-part seal extension portion.

12. A packaged medical device comprising:
a medical device packaging container comprising:
a tray having an upper end opening portion and a medical device storage portion, and
a sheet-like lid portion that closes the upper end opening portion of the tray, wherein:
the tray comprises an annular flange portion located at an entire periphery of the upper end opening portion,
the packaging container comprises an annular heat seal portion that peelably fixes the sheet-like lid portion on the annular flange portion and has a rectangular outer edge,
the annular heat seal portion comprises a first-side seal portion and a second-side seal portion, which are opposite to each other, and a third-side seal portion and a fourth-side seal portion, which are positioned between the first-side seal portion and the second-side seal portion and opposite to each other,
the sheet-like lid portion comprises a flap portion protruding from the first-side seal portion of the annular heat seal portion,
a first end of the third-side seal portion and a first end of the fourth-side seal portion are positioned on a second-side seal portion side by a predetermined length with respect to the first-side seal portion, the first-side seal portion includes a central seal portion, a first side-part seal portion extending obliquely and connecting a first end of the central seal portion with the first end of the third-side seal portion, and a second side-part seal portion extending obliquely and connecting a second end of the central seal portion with the first end of the fourth-side seal portion, the first-side seal portion includes a plurality of central seal extension portions extending from an outer edge of the central seal portion and separated from each other by a predetermined length, a first side-part seal extension portion extending from an outer edge of the first side-part seal portion, and a second side-part seal extension portion extending from an outer edge of the second side-part seal portion, an outer edge of a distal end portion of each central seal extension portion, an outer edge of a distal end portion of the first side-part seal extension portion, and an outer edge of a distal end portion of the second side-part seal extension portion have a rounded shape without corners, and a distance between the first end and the second end of the central seal portion is in a range from 45/100 to 55/100 of a distance between an outer edge of the first end of the third-side seal portion and an outer edge of the first end of the fourth-side seal portion; and a medical device stored in the medical device storage portion of the tray, wherein the upper end opening portion of the tray is peelably sealed by the sheet-like lid portion.

13. The packaged medical device according to claim 12, wherein the medical device is a self-administration prefilled syringe.

14. A medical device packaging container comprising:
a tray having an upper end opening portion and a medical device storage portion; and
a sheet-like lid portion that closes the upper end opening portion of the tray; wherein:
the tray comprises an annular flange portion located at an entire periphery of the upper end opening portion;
the packaging container comprises an annular heat seal portion that peelably fixes the sheet-like lid portion on the annular flange portion and has a rectangular outer edge;
the annular heat seal portion comprises a first-side seal portion and a second-side seal portion, which are opposite to each other, and a third-side seal portion and a fourth-side seal portion, which are positioned between the first-side seal portion and the second-side seal portion and opposite to each other;
the sheet-like lid portion comprises a flap portion protruding from the first-side seal portion of the annular heat seal portion;

a first end of the third-side seal portion and a first end of the fourth-side seal portion are positioned on a second-side seal portion side by a predetermined length with respect to the first-side seal portion;

the first-side seal portion includes a central seal portion, a first side-part seal portion extending obliquely and connecting a first end of the central seal portion with the first end of the third-side seal portion, and a second side-part seal portion extending obliquely and connecting a second end of the central seal portion with the first end of the fourth-side seal portion;

the first-side seal portion includes a plurality of central seal extension portions extending from an outer edge of the central seal portion and separated from each other by a predetermined length, a first side-part seal extension portion extending from an outer edge of the first side-part seal portion, and a second side-part seal extension portion extending from an outer edge of the second side-part seal portion;

an outer edge of a distal end portion of each central seal extension portion, an outer edge of a distal end portion of the first side-part seal extension portion, and an outer edge of a distal end portion of the second side-part seal extension portion have a rounded shape without corners.

15. The medical device packaging container according to claim 14, wherein lengths of the first-side seal portion and the second-side seal portion are less than lengths of the third-side seal portion and the fourth-side seal portion.

16. The medical device packaging container according to claim 14, wherein the third-side seal portion and the fourth-side seal portion are parallel to each other.

17. The medical device packaging container according to claim 14, wherein the third-side seal portion and the fourth-side seal portion are orthogonal to the central seal portion and the second-side seal portion.

18. The medical device packaging container according to claim 14, wherein an inclination angle of a virtual line connecting the first end of the central seal portion with the first end of the third-side seal portion with respect to the third-side seal portion is in a range from 30 degrees to 60 degrees.

19. The medical device packaging container according to claim 18, wherein an inclination angle of a virtual line connecting the second end of the central seal portion with the first end of the fourth-side seal portion with respect to the fourth-side seal portion is in a range from 30 degrees to 60 degrees.

20. The medical device packaging container according to claim 14, wherein a distance between the first end and the second end of the central seal portion is substantially equal to a distance between the first end of the central seal portion and the first end of the third-side seal portion.

\* \* \* \* \*